United States Patent
Del Cardayre et al.

(10) Patent No.: US 10,900,057 B2
(45) Date of Patent: Jan. 26, 2021

(54) RECOMBINANT MICROORGANISMS FOR THE PRODUCTION OF FATTY AMINES

(71) Applicant: Genomatica, Inc., San Diego, CA (US)

(72) Inventors: Stephen B. Del Cardayre, South San Francisco, CA (US); Louis G. Hom, South San Francisco, CA (US)

(73) Assignee: Genomatica, Inc., San Diego, CA (US)

( * ) Notice: Subject to any disclaimer, the term of this patent is extended or adjusted under 35 U.S.C. 154(b) by 657 days.

(21) Appl. No.: 15/039,052

(22) PCT Filed: Dec. 5, 2014

(86) PCT No.: PCT/US2014/068950
§ 371 (c)(1),
(2) Date: May 25, 2016

(87) PCT Pub. No.: WO2015/085271
PCT Pub. Date: Jun. 11, 2015

(65) Prior Publication Data
US 2019/0032097 A1    Jan. 31, 2019

Related U.S. Application Data

(60) Provisional application No. 61/912,184, filed on Dec. 5, 2013.

(51) Int. Cl.
| | | |
|---|---|---|
| *C12P 13/00* | (2006.01) | |
| *C12N 9/16* | (2006.01) | |
| *C12N 9/02* | (2006.01) | |
| *C12N 9/10* | (2006.01) | |
| *C12N 9/00* | (2006.01) | |
| *C12N 9/06* | (2006.01) | |

(52) U.S. Cl.
CPC .......... *C12P 13/001* (2013.01); *C12N 9/0008* (2013.01); *C12N 9/0014* (2013.01); *C12N 9/1096* (2013.01); *C12N 9/16* (2013.01); *C12N 9/93* (2013.01); *C12Y 102/01* (2013.01); *C12Y 102/01042* (2013.01); *C12Y 104/09001* (2013.01); *C12Y 206/01019* (2013.01); *C12Y 206/01082* (2013.01); *C12Y 301/02* (2013.01); *C12Y 602/01003* (2013.01)

(58) Field of Classification Search
None
See application file for complete search history.

(56) References Cited

U.S. PATENT DOCUMENTS

| | | |
|---|---|---|
| 7,169,588 B2 | 1/2007 | Burch et al. |
| 8,097,439 B2 | 1/2012 | Alibhai et al. |
| 8,232,924 B2 | 7/2012 | Bucca et al. |
| 8,268,599 B2 | 9/2012 | Schirmer et al. |
| 9,683,247 B2 * | 6/2017 | Lutes ............ C12Y 203/01086 |
| 2013/0035513 A1 | 2/2013 | Hu et al. |

FOREIGN PATENT DOCUMENTS

| | | |
|---|---|---|
| JP | H03-219886 | 9/1991 |
| JP | 2008501323 A | 1/2008 |
| JP | 2009529890 A | 8/2009 |
| KR | 20120034632 A | 12/2012 |
| WO | 2005118814 A2 | 6/2005 |
| WO | WO-2010/062480 A2 | 6/2010 |
| WO | WO-2010/075483 | 7/2010 |
| WO | WO-2011/047101 | 4/2011 |
| WO | WO-2011/100667 A1 | 8/2011 |
| WO | WO-2011/127409 | 10/2011 |
| WO | WO-2013/039563 A1 | 3/2013 |
| WO | WO-2013/090837 | 6/2013 |

OTHER PUBLICATIONS

Graichen et al. J Bacteriol. Jul. 1999;181(14):4216-22. (Year: 1999).*
Weyman et al. PLoS One. 2011;6(5):e20126. Epub May 26, 2011. (Year: 2011).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Altschul et al. "Protein Database Searches Using Compositionally Adjusted Substitution Matrices," (2005) FEBS J. 272(20):5101-5109.
Avelino Corma et al., "Chemical Routes for the Transformation of Biomass into Chemicals," Chemical Reviews, ACS, vol. 107, No. 6, Jan. 1, 2007, pp. 2411-2502.
Braun, "Minireviews—FhuA (TonA), the Career of a Protein," J. Bacteriol. 191(11): 3431-3436 (2009).
Clark, "Regulation of Fatty Acid Degration in *Escherichia coli*: Analysis by Operon Fusion," J Bacteriol. 148(2): 521-526 (1981).
International Preliminary Report on Patentability for PCT/US2014/068950, dated Mar. 8, 2016.
International Search Report issued on PCT/US2014/068950, dated Apr. 28, 2015.
Maniatis et al., "Regulation of Inducible and Tissue-Specific Gene Expression," Science 236: 1237-1245 (1987).
Needleman and Wunsch, "A General Method Applicable to the Search for Similarities in the Amino Acid Sequence of Two Proteins," J. Mol. Biol. 48:443-453 (1970).
Omelchenko et al., "Non-homologous isofunctinal enzymes: A systematic analysis of alterntive solutions in enzyme evolution," (2010) Biol. Direct 5, 20 pages.

(Continued)

*Primary Examiner* — Christian L Fronda

(74) *Attorney, Agent, or Firm* — Harness Dickey & Pierce, PLC

(57) ABSTRACT

The disclosure relates to recombinant microorganisms for the production of fatty amines and derivatives thereof. Further contemplated are cultured recombinant host cells as well as methods of producing fatty amines by employing these host cells.

20 Claims, 3 Drawing Sheets

Specification includes a Sequence Listing.

(56) References Cited

OTHER PUBLICATIONS

Rosenberg, "Multiple Sequence Alignment Accuracy and Evolutionary Distance Estimation," BMC Bioinformatics 6: 278 (2005).
Communication received on European Application 14827593.6, dated May 10, 2017.
Communication issued on EP Application 14827593.6, dated Mar. 7, 2018.
Examination Report issued on Australian Application 2014360086, dated Nov. 2, 2017.
Notice of Acceptance issued on Australian application 2014360086, dated Apr. 6, 2018.
Substantive Examination Adverse Report in MY Patent Application No. PI 2016001018 dated Dec. 11, 2019 (5 pages).
First Office Action in CN Patent Application No. 201480065828.3 dated Mar. 1, 2019 (with English translation) (15 pages).
First Office Action in MX Patent Application No. MX/a/2016/007054 dated Jul. 9, 2019 (with English translation) (7 pages).
Graichen, et al., "Heterologous expression of correctly assembled methylamine dehydrogenase in Rhodobacter sphaeroides", J. Bacteriol, Jul. 1999, vol. 181, No. 14, pp. 4216-4222.
Notice of Allowance in U.S. Appl. No. 15/623,855 dated Apr. 22, 2019.
First Office Action on CN Application No. 201580018870.4, dated Mar. 25, 2019, 12 pages with translation.
Notice of Reasons for Rejection in JP Patent Application No. 2016-561647, dated Mar. 25, 2019, 9 pages with translation.
Preliminary Office Action in BR Patent Application No. 112016012371.9 dated Oct. 23, 2019 (with English translation) (6 pages).
Second Office Action in CN Patent Application No. 201480065828.3 dated Oct. 28, 2019 (with English translation) (14 pages).
First Examination Report in IN Patent Application No. 201617022788 dated Oct. 29, 2019.
Substantive Examination Adverse Report in MY Patent Application No. PI 2016001018 dated Jun. 25, 2020 (3 pages).
Extended European Search Report in EP Patent Application No. 19198410.3 dated Mar. 2, 2020 (9 pages).
Samsonova, et al., "Molecular cloning and characterization of *Escherichia coli* K12 ygjG gene," BMC Microbiology, Biomed Central Ltd, GB, Jan. 31, 2003, vol. 3, No. 2, pp. 1-10.
Accession P0A9Q7; P17547, uniprot (online) URL: https://www.uniprot.org/uniprot/P0A9Q7b0=version=68 (Retrieved Oct. 20, 2020).
Notice of Reasons for Rejection Issued in Corresponding Japanese Application No. 2019124897 dated Aug. 19, 2020.

\* cited by examiner

RECOMBINANT MICROORGANISMS FOR THE PRODUCTION OF FATTY AMINES

CROSS-REFERENCE TO RELATED APPLICATIONS

This application is a 371(c) national stage entry of PCT/US2014/068950, filed Dec. 5, 2014, which claims the benefit of U.S. Provisional Application No. 61/912,184 filed Dec. 5, 2013, the contents of which are hereby incorporated-by-reference in their entireties.

FIELD

The disclosure relates to recombinant microorganisms for the production of fatty amines and derivatives thereof. Further contemplated are recombinant host cells that express biosynthetic proteins that convert fatty aldehydes to fatty amines in vivo. Still encompassed are methods of producing fatty amines by employing the host cells expressing these biosynthetic proteins.

BACKGROUND

Fatty amines are nitrogen derivatives of fatty acids, olefins, or alcohols. They are made from natural fats and oils or from synthetic or petrochemical raw materials. Today, these compounds are produced primarily through the chemical modification of triglycerides such as tallow or vegetable oils (e.g., coconut-, canola-, and rapeseed oil).

Commercially available fatty amines are made of either a mixture of carbon chains or a specific chain length that ranges from $C_8$ to $C_{22}$. In general, they are classified into primary-, secondary-, and tertiary amines, depending on the number of hydrogen atoms of an ammonia molecule replaced by fatty alkyl or methyl groups. Fatty amines are known to be cationic surface-active compounds that strongly adhere to surfaces through either physical or chemical bonding. Many commercial products are prepared using fatty amines as reactive intermediates. For example, they are useful as surfactants and as components of personal care products such as shampoos and conditioners. The largest market for fatty amines is in fabric softeners and detergents. Fatty amines are also used as foaming- and wetting agents, antistatic agent in the textile and plastics industry, lubricants, paint thickeners, oil field chemicals, asphalt emulsifiers, petroleum additives, corrosion inhibitors, gasoline- and fuel oil additives, flotation agents, pigment wetting agents, epoxy curing agents, herbicides, and others (see Visek K. (2003) *Fatty Amines*; Kirk-Othmer Encyclopedia of Chemical Technology).

Producing fatty amines via microbial fermentation provides a number of advantages, such as providing a more consistent composition, manufacturing at a lower cost, and reducing the environmental impact. In addition, it would open up diverse new feedstocks that are beyond the natural fats and oils and synthetic or petrochemical raw materials used today. There is currently no efficient method for microbial production of fatty amines. The disclosure addresses this need.

SUMMARY

One aspect of the disclosure provides a recombinant microorganism for the production of a fatty amine, including an engineered metabolic pathway for converting a fatty aldehyde to a fatty amine. Herein, the recombinant microorganism has an engineered metabolic pathway for converting a fatty aldehyde to a fatty amine that includes an exogenous biosynthetic enzyme that has aminotransferase or amine dehydrogenase activity. In one embodiment, the exogenous biosynthetic enzyme is a putrescine aminotransferase such as YgjG. In another embodiment, the exogenous biosynthetic enzyme is a GABA aminotransferase such as PuuE. YgjG is encoded by a nucleic acid sequence that codes for an ygjG gene that is expressed in the recombinant microorganism or recombinant microbial cell. Similarly, PuuE is encoded by a nucleic acid sequence that codes for a puuE gene that is expressed in the recombinant microorganism or recombinant microbial cell. In another embodiment, the exogenous biosynthetic enzyme is an amine dehydrogenase such as amethylamine dehydrogenase from *Paracoccus denitrificans*. The recombinant microorganism or recombinant microbial cell produces the fatty amine in vivo or inside the cell. The fatty amine is released into a culture medium by the recombinant microorganism or recombinant microbial cell. In one embodiment, the recombinant microorganism or microbial cell is a recombinant bacterial cell.

Another aspect of the disclosure provides a recombinant microorganism for the production of a fatty amine, including a first engineered metabolic pathway for converting a fatty aldehyde to a fatty amine. The recombinant microorganism has a first engineered metabolic pathway for converting a fatty aldehyde to a fatty amine that includes an exogenous biosynthetic enzyme that has aminotransferase or amine dehydrogenase activity (supra). In one embodiment, the recombinant microorganism has another or second engineered metabolic pathway for converting an acyl-ACP or an acyl-CoA to a fatty acid. The second engineered metabolic pathway is optional. Herein, the acyl-ACP or acyl-CoA is converted to a fatty acid by a biosynthetic enzyme having thioesterase activity. In one embodiment, the biosynthetic enzyme having thioesterase activity is encoded by a nucleic acid sequence that codes for a tesA gene that is expressed in the recombinant microorganism or microbial cell. The recombinant microorganism or recombinant microbial cell produces the fatty amine in vivo or inside the cell. The fatty amine is released into a culture medium by the recombinant microorganism or recombinant microbial cell. In one embodiment, the recombinant microorganism or microbial cell is a recombinant bacterial cell.

Another aspect of the disclosure provides a recombinant microorganism for the production of a fatty amine, including a first engineered metabolic pathway for converting a fatty aldehyde to a fatty amine. The recombinant microorganism has a first engineered metabolic pathway for converting a fatty aldehyde to a fatty amine that includes an exogenous biosynthetic enzyme that has aminotransferase or amine dehydrogenase activity (supra). In one embodiment, the recombinant microorganism has another or second engineered metabolic pathway for converting an acyl-ACP or an acyl-CoA to a fatty acid (supra). In another embodiment, the recombinant microorganism has yet another or third engineered metabolic pathway for converting a fatty acid to a fatty aldehyde. This third engineered metabolic pathway is optional and independent of the second engineered metabolic pathway. Herein, the fatty acid is converted to a fatty aldehyde by a biosynthetic enzyme having carboxylic acid reductase (CAR) activity. In one embodiment, the biosynthetic enzyme having CAR activity is encoded by a nucleic acid sequence that codes for a carB gene that is expressed in the recombinant microorganism or microbial cell. The recombinant microorganism or recombinant microbial cell produces the fatty amine in vivo or inside the cell. The fatty amine is released into a culture medium by the recombinant microorganism or recombinant microbial cell. In one embodiment, the recombinant microorganism or microbial cell is a recombinant bacterial cell.

Another aspect of the disclosure provides a recombinant bacterial cell for production of a fatty amine, including one or more expressed genes that encode an exogenous biosynthetic enzyme having thioesterase activity; one or more expressed genes that encode an exogenous biosynthetic enzyme having carboxylic acid reductase activity; and one or more expressed genes that encode an exogenous biosynthetic enzyme having aminotransferase or amine dehydrogenase activity, wherein the recombinant bacterial cell produces a fatty amine in vivo or inside the bacterial cell. The fatty amine is released into a culture medium by the recombinant bacterial cell. Herein, the exogenous biosynthetic enzyme having thioesterase activity converts an acyl-ACP or acyl-CoA to a fatty acid. The exogenous biosynthetic enzyme having carboxylic acid reductase (CAR) activity converts that fatty acid to a fatty aldehyde. The exogenous biosynthetic enzyme having aminotransferase or amine dehydrogenase activity converts that fatty aldehyde to a fatty amine. In one embodiment, the exogenous biosynthetic enzyme having thioesterase activity is encoded by a nucleic acid sequence that codes for a tesA gene. In another embodiment, the exogenous biosynthetic enzyme having CAR activity is encoded by a nucleic acid sequence that codes for a carB gene. In still another embodiment, the exogenous biosynthetic enzyme having aminotransferase activity is a putrescine aminotransferase such as YgjG or a GABA aminotransferase such as PuuE. YgjG is encoded by a nucleic acid sequence that codes for a ygjG gene. PuuE is encoded by a nucleic acid sequence that codes for a puuE gene. In yet another embodiment, the exogenous biosynthetic enzyme having amine dehydrogenase activity is a methylamine dehydrogenase such as a methylamine dehydrogenase from *Paracoccus denitrificans*.

Another aspect of the disclosure provides a recombinant bacterial cell for production of a fatty amine, including one or more expressed genes that encode an exogenous biosynthetic enzyme having thioesterase activity to convert an acyl-ACP or an acyl-CoA to a fatty acid; one or more expressed genes that encode an exogenous biosynthetic enzyme having carboxylic acid reductase (CAR) activity to convert the fatty acid to a fatty aldehyde; and one or more expressed genes that encode an exogenous biosynthetic enzyme having aminotransferase or amine dehydrogenase activity to convert the fatty aldehyde to a fatty amine, wherein the recombinant bacterial cell produces the fatty amine in vivo or inside the cell. In one embodiment, the exogenous biosynthetic enzyme having aminotransferase or amine dehydrogenase activity is a putrescine aminotransferase such as YgjG. In another embodiment, the exogenous biosynthetic enzyme having aminotransferase or amine dehydrogenase activity is a GABA aminotransferase such as PuuE. YgjG is encoded by a nucleic acid sequence that codes for an ygjG gene that is expressed in the recombinant bacterial cell. Similarly, PuuE is encoded by a nucleic acid sequence that codes for a puuE gene that is expressed in the recombinant bacterial cell. In another embodiment, the exogenous biosynthetic enzyme having aminotransferase or amine dehydrogenase activity is an amine dehydrogenase such as amethylamine dehydrogenase of *Paracoccus denitrificans*. In one embodiment, the exogenous biosynthetic enzyme having thioesterase activity is encoded by a nucleic acid sequence that codes for a tesA gene. In another embodiment, the exogenous biosynthetic enzyme having CAR activity is encoded by a nucleic acid sequence that codes for a carB gene. The recombinant bacterial cell produces the fatty amine in vivo or inside the cell. The fatty amine is released into a culture medium by the recombinant bacterial cell.

The disclosure further contemplates a recombinant bacterial cell for the production of a fatty amine, including a first engineered pathway for converting an acyl-ACP or acyl-CoA to a fatty acid; a second engineered metabolic pathway for converting the fatty acid to a fatty aldehyde; and a third engineered metabolic pathway for converting the fatty aldehyde to a fatty amine, wherein the recombinant bacterial cell produces the fatty amine in vivo or inside the cell. In one embodiment, the acyl-ACP or acyl-CoA is converted to a fatty acid by an exogenously expressed biosynthetic enzyme having thioesterase activity; the fatty acid is converted to a fatty aldehyde by an exogenously expressed biosynthetic enzyme having carboxylic acid reductase (CAR) activity; and the fatty aldehyde is converted to a fatty amine by an exogenously expressed biosynthetic enzyme having aminotransferase or amine dehydrogenase activity. In one embodiment, the exogenous biosynthetic enzyme having aminotransferase or amine dehydrogenase activity is a putrescine aminotransferase such as YgjG. In another embodiment, the exogenous biosynthetic enzyme having aminotransferase or amine dehydrogenase activity is a GABA aminotransferase such as PuuE. YgjG is encoded by a nucleic acid sequence that codes for an ygjG gene that is expressed in the recombinant bacterial cell. Similarly, PuuE is encoded by a nucleic acid sequence that codes for a puuE gene that is expressed in the recombinant bacterial cell. In another embodiment, the exogenous biosynthetic enzyme having aminotransferase or amine dehydrogenase activity is an amine dehydrogenase such as a methylamine dehydrogenase from *Paracoccus denitrificans*. In one embodiment, the exogenous biosynthetic enzyme having thioesterase activity is encoded by a nucleic acid sequence that codes for a tesA gene. In another embodiment, the exogenous biosynthetic enzyme having CAR activity is encoded by a nucleic acid sequence that codes for a carB gene. The recombinant bacterial cell produces the fatty amine in vivo or inside the cell. The fatty amine is released into a culture medium by the recombinant bacterial cell.

Another aspect of the disclosure provides a recombinant microorganism for the production of a fatty amine, including but not limited to, *Escherichia, Bacillus, Cyanophyta, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* and *Streptomyces*. In one embodiment, *Escherichia* is *Escherichia coli*. In another embodiment, *Cyanophyta* includes, but is not limited to, *Prochlorococcus, Synechococcus, Synechocystis, Cyanothece,* and *Nostoc punctiforme*. In still another embodiment, *Cyanophyta* includes, but is not limited to, *Synechococcus elongatus* PCC7942, *Synechocystis* sp. PCC6803, and *Synechococcus* sp. PCC7001.

Another aspect of the disclosure provides a method of producing a fatty amine, comprising culturing a recombinant microorganism in a fermentation broth containing a carbon source. The microorganism encompasses at least one engineered metabolic pathway for producing a fatty amine in vivo (supra). Another aspect of the disclosure provides a method of producing a fatty amine in a recombinant bacterial cell, including culturing a cell that expresses an engineered metabolic pathway for producing a fatty amine (supra) in a fermentation broth in the presence of a carbon source; and harvesting fatty amines that collect in the fermentation broth.

The disclosure further encompasses a cell culture including a recombinant microbial cell for the production of amines (supra). In one embodiment, the cell culture encompasses a recombinant bacterial cell for the production of amines. In another embodiment, the recombinant microbial cell is a recombinant bacterial cell.

Another aspect of the disclosure provides a recombinant microorganism that has an engineered metabolic pathway for fatty aldehyde production and a biosynthetic enzyme that converts a fatty aldehyde to a fatty amine, wherein the biosynthetic enzyme has aminotransferase/transaminase or amine dehydrogenase activity. In one embodiment, the biosynthetic enzyme is a putrescine aminotransferase or a GABA aminotransferase. In another embodiment, the biosynthetic enzyme is an amine dehydrogenase or an amine oxidase.

Another aspect of the disclosure provides a recombinant microorganism that has an engineered metabolic pathway for fatty aldehyde production and an engineered metabolic pathway for fatty amine production including a biosynthetic enzyme that converts a fatty aldehyde to a fatty amine, wherein the recombinant microorganism is a microbial cell. In one aspect, the microbial cell is a recombinant cell. The microbial cell includes, but is not limited to, *Escherichia, Bacillus, Cyanophyta, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* and *Streptomyces*. In one embodiment, *Escherichia* is *Escherichia coli*. In another embodiment, *Cyanophyta* includes, but is not limited to, *Prochlorococcus, Synechococcus, Synechocystis, Cyanothece,* and *Nostoc punctiforme*. In another particular embodiment, *Cyanophyta* is *Synechococcus elongatus* PCC7942, *Synechocystis* sp. PCC6803, or *Synechococcus* sp. PCC7001.

Another aspect of the disclosure provides a recombinant microorganism that has an engineered metabolic pathway for fatty aldehyde production and an engineered metabolic pathway for fatty amine production. In one embodiment, the engineered metabolic pathway for fatty aldehyde production includes a thioesterase and/or a carboxylic acid reductase (CAR) that convert a fatty acid to a fatty aldehyde, while the engineered metabolic pathway for fatty amine production includes an aminotransferase/transaminase or amine dehydrogenase that converts a fatty aldehyde to a fatty amine. In some embodiments, the thioesterase is encoded by a nucleic acid sequence that codes for a tesA gene with or without leader sequence while the carboxylic acid reductase (CAR) is encoded by a nucleic acid sequence that codes for a carB gene both of which are expressed in the microorganism. In one embodiment, the aminotransferase/transaminase is a putrescine aminotransferase or a GABA aminotransferase. In one embodiment, the putrescine aminotransferase is YgjG which is encoded by a nucleic acid sequence that codes for an ygjG gene that is expressed in the microorganism. In another embodiment, the GABA aminotransferase is PuuE which is encoded by a nucleic acid sequence that codes for a puuE gene that is expressed in the microorganism. In still another embodiment, the amine dehydrogenase is a methylamine dehydrogenase from *Paracoccus denitrificans*. In one embodiment, the fatty amine is released into the supernatant or culture media by the microorganism. In another embodiment, the fatty amine is collected from inside the microorganism where it can be extracted during or after a fermentation procedure.

The disclosure further contemplates a method of producing a fatty amine, including culturing a recombinant microorganism in a fermentation broth containing a carbon source, wherein the recombinant microorganism contains an engineered metabolic pathway for fatty aldehyde production and a biosynthetic enzyme that converts a fatty aldehyde to a fatty amine, wherein the biosynthetic enzyme has aminotransferase or amine dehydrogenase activity, and wherein the microorganism produces a fatty amine in vivo.

The disclosure further encompasses a recombinant microbial cell that includes expression of one or more enzymes having thioesterase and carboxylic acid reductase (CAR) activity; and expression of an enzyme having aminotransferase or amine dehydrogenase activity, wherein the microbial cell produces fatty amines. In one embodiment, the biosynthetic enzyme is a putrescine aminotransferase such as YgjG or a GABA aminotransferase such as PuuE. In another embodiment, the biosynthetic enzyme is an amine dehydrogenase such as a methylamine dehydrogenase from *Paracoccus denitrificans*. In yet another embodiment, the biosynthetic enzyme is an amine oxidase.

Still, another aspect of the disclosure provides a method for producing a fatty amine in a recombinant microorganism. The method includes culturing a microbial cell (supra) in a fermentation medium in the presence of a carbon source; and harvesting the fatty amines that collect in the supernatant or fermentation medium. The recombinant microbial cell expresses an engineered metabolic pathway for fatty aldehyde production and a biosynthetic enzyme that converts a fatty aldehyde to a fatty amine, wherein the biosynthetic enzyme has aminotransferase or amine dehydrogenase activity. In another aspect, the recombinant microbial cell expresses an engineered metabolic pathway for fatty aldehyde production and an engineered metabolic pathway for amine production including a biosynthetic enzyme that converts a fatty aldehyde to a fatty amine, wherein the biosynthetic enzyme has aminotransferase or amine dehydrogenase activity.

Another aspect of the disclosure provides a fatty amine derived from a carbon source that is not a petrochemical raw material. For example, the disclosure provides for fatty amines derived from renewable feedstocks, such as $CO_2$, CO, glucose, sucrose, xylose, arabinose, glycerol, mannose, or mixtures thereof. Other feedstocks provided herein from which fatty amines may be derived include starches, cellulosic biomass, molasses, and other sources of carbohydrates including carbohydrate mixtures derived from hydrolysis of cellulosic biomass, or the waste materials derived from plant- or natural oil processing.

BRIEF DESCRIPTION OF THE FIGURES

The present disclosure is best understood when read in conjunction with the accompanying figures, which serve to illustrate the preferred embodiments. It is understood, however, that the disclosure is not limited to the specific embodiments disclosed in the figures.

DETAILED DESCRIPTION

General Overview

Figure 1:
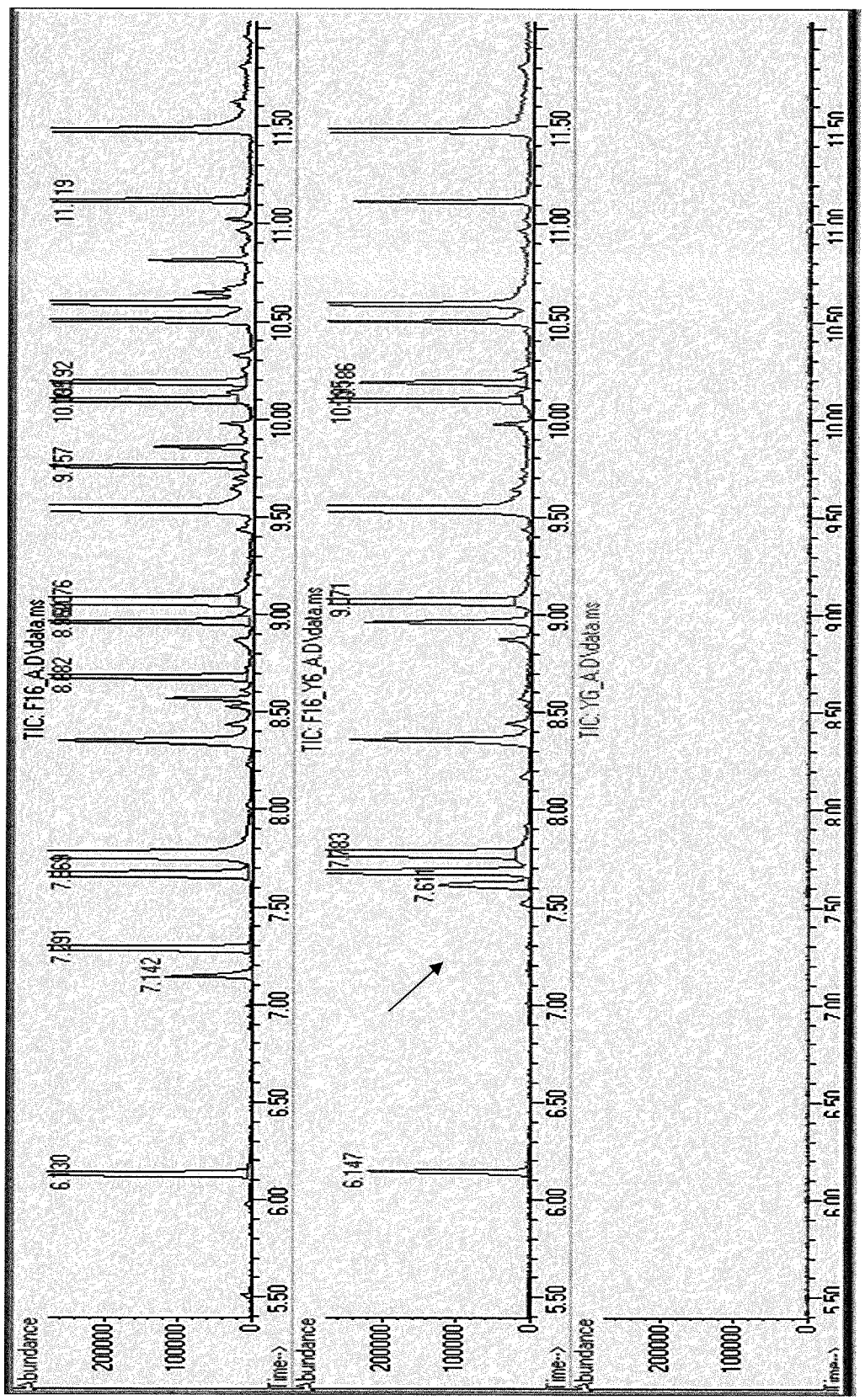
FIG. 1 is a MS/GC chromatograph from microbial cell extracts showing a unique fatty amine peak (see middle panel at 7.61 minutes, marked with an arrow) produced via expression of a thioesterase, a carboxylic acid reductase, and an aminotransferase/transaminase (middle row). The top row is the F16 negative control; the middle row is the F16-YG sample; and the bottom row is the YG negative control. Additional peaks in the top and middle rows are fatty alcohols.

The disclosure relates to microbial production of fatty amines, which represent a new class of renewable chemical products. The fatty amines are produced through a microorganism that expresses an engineered metabolic pathway to convert fatty aldehydes to fatty amines. As such, the microorganism expresses at least one exogenous biosynthetic enzyme in order to produce fatty amines in vivo. The exogenous biosynthetic enzyme may have aminotransferase or amine dehydrogenase activity; or carboxylic acid reductase (CAR) activity; or thioesterase activity or a combination thereof. Alternative forms of the enzymatic activity are also encompassed herein.

Definitions

As used in this specification and the appended claims, the singular forms "a," "an" and "the" include plural referents unless the context clearly dictates otherwise. Thus, for example, reference to "a host cell" includes two or more such host cells, reference to "a fatty amine" includes one or more fatty amines, or mixtures of amines, reference to "a nucleic acid sequence" includes one or more nucleic acid sequences, reference to "an enzyme" includes one or more enzymes, and the like.

The term "engineered metabolic pathway" refers to one or more genetically engineered or optimized chemical reaction(s) catalyzed by at least one biosynthetic enzyme expressed in a cell in order to produce (or increase production of) a certain substance (i.e., a precursor, an intermediate or an end product) inside that cell. In one embodiment, the biosynthetic enzyme is an exogenous biosynthetic enzyme. In another embodiment, the engineered metabolic pathway permits the cell's production of a desired end product. In another embodiment, the engineered metabolic pathway permits the cell's production of a desired precursor. In another embodiment, the engineered metabolic pathway permits the cell's production of a desired intermediate.

The term "in vivo" refers to "inside the cell" when used in context of producing a specific product. For example, production of fatty amines in vivo means production of fatty amines inside the cell.

Sequence Accession numbers as referred to herein were obtained from databases provided by the NCBI (National Center for Biotechnology Information) maintained by the National Institutes of Health, U.S.A. (which are identified herein as "NCBI Accession Numbers" or alternatively as "GenBank Accession Numbers"), and from the UniProt Knowledgebase (UniProtKB) and Swiss-Prot databases provided by the Swiss Institute of Bioinformatics (which are identified herein as "UniProtKB Accession Numbers").

Enzyme Classification (EC) Numbers are established by the Nomenclature Committee of the International Union of Biochemistry and Molecular Biology (IUBMB), a description of which is available on the IUBMB Enzyme Nomenclature website on the World Wide Web. EC numbers classify enzymes according to the enzyme-catalyzed reactions. For example, if different enzymes (e.g., from different organisms) catalyze the same reaction, then they are classified under the same EC number. In addition, through convergent evolution, different protein folds can catalyze identical reactions and therefore are assigned identical EC numbers (see Omelchenko et al. (2010) *Biol. Direct* 5:31). Proteins that are evolutionarily unrelated and can catalyze the same biochemical reactions are sometimes referred to as analogous enzymes (i.e., as opposed to homologous enzymes). EC numbers differ from, for example, UniProt identifiers which specify a protein by its amino acid sequence.

As used herein, the term "nucleotide" refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

The term "polynucleotide" refers to a polymer of ribonucleotides (RNA) or deoxyribonucleotides (DNA), which can be single-stranded or double-stranded and which can contain non-natural or altered nucleotides. The terms "polynucleotide," "nucleic acid sequence," and "nucleotide sequence" are used interchangeably herein and refer to a polymeric form of nucleotides of any length. These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to, plasmid, viral, chromosomal, EST, cDNA, mRNA, and rRNA.

As used herein, the terms "polypeptide" and "protein" are used interchangeably to refer to a polymer of amino acid residues. The term "recombinant polypeptide" refers to a polypeptide that is produced by recombinant techniques, wherein generally cDNA or RNA encoding the expressed protein is inserted into a suitable expression vector that is in turn used to transform a host cell to produce the polypeptide. Similarly, the terms "recombinant polynucleotide" or "recombinant nucleic acid" or "recombinant DNA" are produced by recombinant techniques that are known to those of skill in the art.

As used herein, the terms "homolog," and "homologous" refer to a polynucleotide or a polypeptide comprising a sequence that is at least about 50 percent (%) identical to the corresponding polynucleotide or polypeptide sequence.

Preferably homologous polynucleotides or polypeptides have polynucleotide sequences or amino acid sequences that have at least about 80%, 81%, 82%, 83%, 84%, 85%, 86%, 87%, 88%, 89%, 90%, 91%, 92%, 93%, 94%, 95%, 96%, 97%, 98% or at least about 99% homology to the corresponding amino acid sequence or polynucleotide sequence. As used herein the terms sequence "homology" and "sequence identity" are used interchangeably.

One of ordinary skill in the art is well aware of methods to determine homology between two or more sequences. Briefly, calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In one preferred embodiment, the length of a first sequence that is aligned for comparison purposes is at least about 30%, preferably at least about 40%, more preferably at least about 50%, even more preferably at least about 60%, and even more preferably at least about 70%, at least about 80%, at least about 85%, at least about 90%, at least about 95%, at least about 98%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position. The percent homology between the two sequences is a function of the number of identical positions shared by the sequences, taking into account the number of gaps and the length of each gap, that need to be introduced for optimal alignment of the two sequences. The comparison of sequences and determination of percent homology between two sequences can be accomplished using a mathematical algorithm, such as BLAST (Altschul et al. (1990) *J. Mol. Biol.* 215(3):403-410). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch (1970) *J. Mol. Biol.* 48:444-453). The percent homology between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnological arts (see, e.g., Rosenberg (2005) *BMC Bioinformatics* 6:278; Altschul et al. (2005) *FEBS J.* 272(20):5101-5109).

The term "hybridizes under low stringency, medium stringency, high stringency, or very high stringency conditions" describes conditions for hybridization and washing. Guidance for performing hybridization reactions can be found in biotechnological texts (e.g., see Current Protocols in Molecular Biology, John Wiley & Sons, N.Y. (1989), 6.3.1-6.3.6, where aqueous and non-aqueous methods are described in detail and either method can be used). For example, specific hybridization conditions are as follows: (1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions—6×SSC at about 45° C., followed by one or more washes in 0.2×SSC, 0.1% SDS at 60° C.; (3) high stringency hybridization conditions—6×SSC at about 45° C., followed by one or more washes in 0.2.×SSC, 0.1% SDS at 65° C.; and (4) very high stringency hybridization conditions—0.5M sodium phosphate, 7% SDS at 65° C., followed by one or more washes at 0.2×SSC, 1% SDS at 65° C. Very high stringency conditions (4) are generally the preferred conditions unless otherwise specified.

The term "endogenous" means "originating within". As such, an "endogenous" polypeptide refers to a polypeptide that is encoded by the native genome of the host cell. For example, an endogenous polypeptide can refer to a polypeptide that is encoded by the genome of the parental microbial cell (e.g., the parental host cell) from which the recombinant cell is engineered (or derived).

The term "exogenous" means "originating from outside". As such, an "exogenous" polypeptide refers to a polypeptide which is not encoded by the native genome of the cell. An exogenous polypeptide and/or exogenous polynucleotide can be transferred into the cell and can be cloned from or derived from a different cell type or species; or can be cloned from or derived from the same cell type or species. For example, an "exogenous biosynthetic enzyme" is an example of an exogenous polypeptide, wherein the polypeptide codes for an enzyme having a certain enzymatic activity. In another example, a variant (i.e., mutant or altered) polypeptide is an example of an exogenous polypeptide. Similarly, a non-naturally-occurring nucleic acid molecule is considered to be exogenous to a cell once introduced into the cell. The term "exogenous" may also be used with reference to a polynucleotide, polypeptide, or protein which is present in a recombinant host cell in a non-native state. For example, an "exogenous" polynucleotide, polypeptide or protein sequence may be modified relative to the wild type sequence naturally present in the corresponding wild type host cell, e.g., a modification in the level of expression or in the sequence of a polynucleotide, polypeptide or protein. Along those same lines, a nucleic acid molecule that is naturally-occurring can also be exogenous to a particular cell. For example, an entire coding sequence isolated from cell X is an exogenous nucleic acid with respect to cell Y once that coding sequence is introduced into cell Y, even if X and Y are the same cell type.

The term "overexpressed" means that a gene is caused to be transcribed at an elevated rate compared to the endogenous transcription rate for that gene. In some examples, overexpression additionally includes an elevated rate of translation of the corresponding protein compared to the endogenous translation rate for that protein. In some embodiments, the term "overexpress" means to express a polynucleotide or polypeptide in a cell at a greater concentration than is normally expressed in a corresponding wild-type cell under the same conditions. Methods of testing for overexpression are well known in the art, for example transcribed RNA levels can be assessed using rtPCR and protein levels can be assessed using SDS page gel analysis.

The term "heterologous" means "derived from a different organism, different cell type, and/or different species". As used herein, the term "heterologous" is typically associated with a polynucleotide or a polypeptide or a protein and refers to a polynucleotide, a polypeptide or a protein that is not naturally present in a given organism, cell type, or species. For example, a polynucleotide sequence from a plant can be introduced into a microbial host cell by recombinant methods, and the plant polynucleotide is then heterologous to that recombinant microbial host cell. Similarly, a polynucleotide sequence from cyanobacteria can be introduced into a microbial host cell of the genus *Escherichia* by recombinant methods, and the polynucleotide from cyanobacteria is then heterologous to that recombinant microbial host cell. Along those lines, a "heterologous biosynthetic enzyme" is an example of a heterologous polypeptide, wherein the polypeptide codes for an enzyme having a certain enzymatic activity.

As used herein, the term "fragment" of a polypeptide refers to a shorter portion of a full-length polypeptide or protein ranging in size from two amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

The term "mutagenesis" refers to a process by which the genetic information of an organism is changed in a stable manner. Mutagenesis of a protein coding nucleic acid sequence produces a mutant protein. Mutagenesis also refers to changes in non-coding nucleic acid sequences that result in modified protein activity.

A "mutation", as used herein, refers to a permanent change in a nucleic acid position of a gene or in an amino acid position of a polypeptide or protein. Mutations include substitutions, additions, insertions, and/or deletions. For example, a mutation in an amino acid position can be a substitution of one type of amino acid with another type of amino acid (e.g., a serine (S) may be substituted with an alanine (A); a lysine (L) may be substituted with an T (Threonine); etc.). As such, a polypeptide or a protein can have one or more mutations wherein one amino acid is substituted with another amino acid. For example, a biosynthetic polypeptide or protein can have one or more mutations in its amino acid sequence.

The term "biosynthetic enzyme" as used herein, refers to a protein that has an enzymatic activity that is related to fatty acid derivative biosynthesis (e.g., fatty acids, fatty aldehydes, fatty alcohols, fatty amines, fatty esters, etc.). An example of a biosynthetic enzyme as used herein is an enzyme that can convert a fatty aldehyde precursor to a fatty amine (e.g., a fatty amine producing biosynthetic enzyme). Another example of a biosynthetic enzyme as used herein is an enzyme that can convert a fatty acid to a fatty aldehyde (e.g., a fatty aldehyde producing biosynthetic enzyme). Still another example of a biosynthetic enzyme as used herein is an enzyme that can convert an acyl-ACP or acyl-CoA to a fatty acid (e.g., a fatty acid producing biosynthetic enzyme). When a cell has been transformed with a biosynthetic enzyme it is a cell that expresses the biosynthetic enzyme (e.g., a recombinant cell). In one embodiment, the titer and/or yield of a fatty amine related compound produced by a cell that expresses a fatty amine producing biosynthetic enzyme is at least twice that of a corresponding wild type cell (i.e., a corresponding cell that does not express the fatty amine producing biosynthetic enzyme). In another embodiment, the titer and/or yield of a fatty amine related compound produced by a cell that expresses the fatty amine producing biosynthetic enzyme is at least about 1 times, at least about 2 times, at least about 3 times, at least about 4 times, at least about 5 times, at least about 6 times, at least about 7 times, at least about 8 times, at least about 9 times, or at least about 10 times greater than that of a corresponding wild type cell. In one embodiment, the titer and/or yield of a fatty amine related compound produced by a cell expressing a fatty amine producing biosynthetic enzyme is at least about 1 percent, at least about 2 percent, at least about 3 percent, at least about 4 percent, at least about 5 percent, at least about 6 percent, at least about 7 percent, at least about 8 percent, at least about 9 percent, or about 10 percent greater than that of a corresponding wild type cell. In another embodiment, the titer and/or yield due to the expression of a fatty amine producing biosynthetic enzyme is at least about 20 percent to at least about 100 percent greater than that of the wild type cell. In another embodiments, the titer and/or yield of a fatty amine related compound produced by a cell due to the expression of a fatty amine producing biosynthetic enzyme is at least about 20 percent, at least about 25 percent, at least about 30 percent, at least about 35 percent, at least about 40 percent, at least about 45 percent at least about 50 percent, at least about 55 percent, at least about 60 percent, at least about 65 percent, at least about 70 percent, at least about 75 percent, at least about 80 percent, at least about 85 percent, at least about 90 percent, at least about 95 percent, at least about 97 percent, at least about 98 percent, or at least about 100 percent greater than that of the corresponding wild type cell.

As used herein, the term "gene" refers to nucleic acid sequences encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g., such sequences include but are not limited to ribosome binding sites or translational control sequences).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., *Science*, 236: 1237-1245 (1987)). Exemplary expression control sequences are described in biotechnological texts (e.g., see Goeddel, Gene Expression Technology: Methods in Enzymology, Vol. 185, Academic Press, San Diego, Calif. (1990)). In the methods of the present disclosure, one or more expression control sequences are operably linked to one or more polynucleotide sequences. By "operably linked" is meant that a polynucleotide sequence and an expression control sequence are connected in such a way as to permit gene expression when the appropriate molecules (e.g., transcriptional activator proteins) are bound to the expression control sequence. Operably linked promoters are located upstream of the selected polynucleotide sequence in terms of the direction of transcription and translation. Operably linked enhancers can be located upstream, within, or downstream of the selected polynucleotide.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. Other useful expression vectors are provided in linear form. Also included are such other forms of expression vectors that serve equivalent functions and that have become known in the art subsequently hereto. In some embodiments, a recombinant vector further includes a promoter operably linked to the polynucleotide sequence. In some embodiments, the promoter is a developmentally-regulated promoter, an organelle-specific promoter, a tissue-specific promoter, an inducible promoter, a constitutive promoter, or a cell-specific promoter. The recombinant vector typically comprises at least one sequence selected from an expression control sequence operatively coupled to the polynucleotide sequence; a selection marker operatively coupled to the polynucleotide sequence; a marker sequence operatively coupled to the polynucleotide sequence; a purification moiety operatively coupled to the polynucleotide sequence; a secretion sequence operatively coupled to the polynucleotide sequence; and a targeting sequence operatively coupled to the polynucleotide sequence. In certain embodiments, the nucleotide sequence is stably incorporated into the genomic DNA of the host cell, and the expression of the nucleotide sequence is under the control of a regulated promoter region. The expression vectors as used herein include a particular polynucleotide sequence as described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein.

The terms "recombinant cell" and "recombinant host cell" are used interchangeably herein and refer to a cell that has been modified to exogenously express at least one biosynthetic enzyme. In one particular embodiment, the biosynthetic enzyme can convert a fatty aldehyde precursor into a fatty amine. Thus, in one embodiment, the recombinant cell encompasses a biosynthetic enzyme that can increase the specific activity of the recombinant cell to produce fatty amines or fatty amine derived compounds. A recombinant cell can be derived from a microorganism or microbial cell such as a bacterium, a virus or a fungus. The recombinant cell can be used to produce fatty amines. In some embodiments, the recombinant cell exogenously expresses one or more polynucleotide(s), each polynucleotide encoding a polypeptide having biosynthetic enzyme activity, wherein the recombinant cell produces a fatty amine related composition when cultured in the presence of a carbon source under conditions effective to express the polynucleotide(s).

As used herein, the term "microorganism" refers to a microscopic organism. Examples of a microorganism are a bacterium, a virus, or a fungus. In one embodiment, a microorganism is a bacterial cell. In another embodiment, a microorganism is a prokaryote or prokaryotic cell. In yet another embodiment, a microorganism is a fungal cell such as a yeast cell. In another embodiment, a microorganism is a viral cell. In a related embodiment, a "recombinant microorganism" is a microorganism that has been genetically altered and expresses or encompasses an exogenous and/or heterologous nucleic acid sequence. In another related embodiment, a "recombinant microorganism" is a microorganism that has been genetically altered and expresses an engineered metabolic pathway that includes at least one exogenously expressed protein (e.g., an exogenous biosynthetic enzyme).

The term "acyl-ACP" refers to an acyl thioester formed between the carbonyl carbon of the alkyl chain and the sulfhydryl group of the phosphopantetheinyl moiety of an acyl carrier protein (ACP). The phosphopantetheinyl moiety is post-translationally attached to a conserved serine residue on the ACP by the action of holo-acyl carrier protein synthase (ACPS), a phosphopantetheinyl transferase. In some embodiments an acyl-ACP is an intermediate in the synthesis of fully saturated acyl-ACPs. In other embodiments an acyl-ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-ACPs are substrates for enzymes that convert them to fatty acid derivatives.

The term "acyl-CoA" is a temporary compound formed when coenzyme A (CoA) attaches to the end of a fatty acid inside a living cell. It refers to a group of coenzymes that are involved in the metabolism of fatty acids. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-CoAs are substrates for enzymes that convert them to fatty acid derivatives.

The term "metabolic pathway for fatty aldehyde production" means any biosynthetic pathway that produces fatty aldehydes. The metabolic pathway for fatty aldehyde production may include any number of enzymes to produce fatty aldehydes.

The term "metabolic pathway for fatty amine production" means any biosynthetic pathway that produces fatty amines. The metabolic pathway for fatty amine production may include at least one enzyme to produce fatty amines.

As used herein, "fatty amine" means an amine having the formula RNH2. A fatty amine as referred to herein can be any fatty amine made from, for example, a fatty acid or fatty aldehyde or fatty aldehyde derived from a fatty acyl-ACP. In some embodiments, the R group is at least 5, at least 6, at least 7, at least 8, at least 9, at least 10, at least 11, at least 12, at least 13, at least 14, at least 15, at least 16, at least 17, at least 18, or at least 19 carbons in length. Alternatively, or in addition, the R group is 24 or less, 23 or less, 22 or less, 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty amine composition comprises one or more of a C6, C7, C8, C9, C10, C11, C12, C13, C14, C15, C16, C17, C18, C19, C20, C21, 22, 23, and a C24 fatty amine. In other embodiments, the fatty amine composition includes one or more of a C6, C7, C8, C9, C10, C11, C12, C13, C14, C15, C16, C17, and a C18 fatty amine. In still other embodiments, the fatty amine composition includes C12, C14, C16 and C18 fatty amines; C12, C14 and C16 fatty amines; C14, C16 and C18 fatty amines; or C12 and C14 fatty amines. The R group of a fatty amine, can be a straight chain or a branched chain. Branched chains may have more than one point of branching and may include cyclic branches. In some embodiments, the branched fatty amine is a C6, C7, C8, C9, C10, C11, C12, C13, C14, C15, C16, C17, C18, C19, C20, C21, C22, C23 or C24 branched fatty amine. The R group of a branched or unbranched fatty amine can be saturated or unsaturated. If unsaturated, the R group can have one or more than one point of unsaturation. In some embodiments, the unsaturated fatty amine is a monounsaturated fatty amine. In certain embodiments, the unsaturated fatty amine is a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1 or a C24:1 unsaturated fatty amine. In certain embodiments, the unsaturated fatty amine is a C10:1, C12:1, C14:1, C16:1, or C18:1 unsaturated fatty amine. In other embodiments, the unsaturated fatty amine is unsaturated at the omega-7 position. In certain embodiments, the unsaturated fatty amine has a cis double bond. Fatty amines are classified into primary-, secondary-, and tertiary amines, depending on the number of hydrogen atoms of an ammonia molecule replaced by fatty alkyl or methyl groups. Examples of fatty amines that can be used as detergents, in water treatments, as flotation agents, in petroleum, as corrosion inhibitors, in textiles, in rubber, and the like, are tertiary amines such as di-methyl alkyl amines (C10, C12, C14, C16 or C18) and di-alkyl methyl amines (C10); and tertiary amine blends such as di-methyl alkyl amines (C8-C18, C12-C18, C12-C14, or C16-C18).

The term "clone" typically refers to a cell or group of cells descended from and essentially genetically identical to a single common ancestor, for example, the bacteria of a cloned bacterial colony arose from a single bacterial cell.

As used herein, the term "culture" typical refers to a liquid media comprising viable cells. In one embodiment, a culture comprises cells reproducing in a predetermined culture media under controlled conditions, for example, a culture of recombinant host cells grown in liquid media comprising a selected carbon source and nitrogen. "Culturing" or "cultivation" refers to growing a population of host cells (e.g., recombinant host cells) under suitable conditions in a liquid or solid medium. In some embodiments, culturing refers to the fermentative bioconversion of a substrate to an end-product. Culturing media are well known and individual components of such culture media are available from commercial sources (e.g., DIFCO media and BBL media). In one example, the aqueous nutrient medium is a "rich medium" including complex sources of nitrogen, salts, and carbon, such as YP medium, including 10 g/L of peptone and 10 g/L yeast extract. In another example, the nutrient medium is a "minimal medium" composed of trace elements, nutrients, and salts.

The terms, "a modified activity" or "an altered level of activity", for example, with respect to an enzymatic activity in a recombinant host cell, refers to a difference in one or more characteristics in the enzyme activity as determined relative to the parent or native host cell. Typically, such differences in activity are determined between a recombinant host cell (i.e., having modified activity) and the corresponding wild-type host cell, particularly by comparing the culture of a recombinant host cell with the culture of the corresponding wild-type host cell. Modified activities can be the result of, for example, modified amounts of protein expressed by a recombinant host cell (e.g., as the result of increased or decreased number of copies of DNA sequences encoding the protein, increased or decreased number of mRNA transcripts encoding the protein, and/or increased or decreased amounts of protein translation of the protein from mRNA); changes in the structure of the protein (e.g., changes to the primary structure, such as, changes to the protein's coding sequence that result in changes in substrate specificity, changes in observed kinetic parameters); and changes in protein stability (e.g., increased or decreased degradation of the protein). In certain instances, the coding sequences for the polypeptides described herein are codon optimized for expression in a particular host cell. For example, for expression in *E. coli*, one or more codons can be optimized accordingly (see Grosjean et al. (1982) *Gene* 18:199-209).

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons). As used herein, the phrase "the expression of said nucleotide sequence is modified relative to the wild type nucleotide sequence," means an increase or decrease in the level of expression and/or activity of an endogenous nucleotide sequence or the expression and/or activity of a heterologous or non-native polypeptide-encoding nucleotide sequence. The terms "altered level of expression" and "modified level of expression" are used interchangeably and mean that a polynucleotide, polypeptide, or hydrocarbon is present in a different concentration in an engineered host cell as compared to its concentration in a corresponding wild-type cell under the same conditions. As used herein, the term "express" with respect to a polynucleotide is to cause it to function. A polynucleotide which encodes a polypeptide (or protein) will, when expressed, be transcribed and translated to produce that polypeptide (or protein).

As used herein, the term "titer" refers to the quantity of a fatty amine or fatty amine related compound or composition produced per unit volume of host cell culture. In any aspect of the compositions and methods described herein, a fatty amine is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty amine is produced at a titer of more than 100 g/L, more than 200 g/L, or more than 300 g/L. One preferred titer of fatty amine produced by a recombinant host cell according to the methods of the disclosure is from 5 g/L to 200 g/L, 10 g/L to 150 g/L, 20 g/L to 120 g/L, and 30 g/L to 100 g/L. The titer may refer to a particular fatty amine or a combination or composition of fatty amines produced by a given recombinant host cell culture. For example, the expression of biosynthetic protein that can convert a fatty aldehyde to a fatty amine in a recombinant host cell such as *E. coli* results in the production of a higher titer as compared to a recombinant host cell expressing the corresponding wild type polypeptide that lacks the expression of the biosynthetic protein that can convert a fatty aldehyde to a fatty amine. In one embodiment, the higher titer ranges from at least about 5 g/L to about 200 g/L.

As used herein, the "yield of a fatty amine related compound including fatty amines produced by a host cell" refers to the efficiency by which an input carbon source is converted to product in a host cell. Host cells engineered to produce a fatty amine or fatty amine related compound according to the methods of the disclosure have a yield of at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% or a range bounded by any two of the foregoing values. In other embodiments, a fatty amine is produced at a yield of more than about 30%, more than about 35%, more than about 40%, more than about 45%, more than about 50%, more than about 55%, more than about 60%, more than about 65%, more than about 70%, more than about 75%, more than about 80%, more than about 85%, more than about 90% or higher. Alternatively, or in addition, the yield is about 30% or less, about 27% or less, about 25% or less, or about 22% or less. In another embodiment, the yield is about 50% or less, about 45% or less, or about 35% or less. In another embodiment, the yield is about 95% or less, or 90% or less, or 85% or less, or 80% or less, or 75% or less, or 70% or less, or 65% or less, or 60% or less, or 55% or less, or 50% or less. Thus, the yield can be bounded by any two of the above endpoints. For example, the yield of a fatty amine or fatty amine related compound produced by the recombinant host cell according to the methods of the disclosure can be about 5% to about 15%, about 10% to about 25%, about 10% to about 22%, about 15% to about 27%, about 18% to about 22%, about 20% to about 28%, about 20% to about 30%, about 30% to about 40%, about 40% to about 50%, about 50% to about 60%, about 60% to about 70%, about 70% to about 80%, about 80% to about 90%, or about 90% to about 100%. The yield may refer to a particular fatty amine or fatty amine related compound or a combination of fatty amines produced by a given recombinant host cell culture. For example, the expression of a biosynthetic protein that can convert a fatty aldehyde to a fatty amine in a recombinant host cell such as *E. coli* results in the production of a higher yield of fatty amines or fatty amine derived compounds including compositions or blends of fatty amines as compared to a host cell expressing the corresponding wild type polypeptide. In one embodiment, the higher yield ranges from about 10% to about 100% of theoretical yield.

As used herein, the term "productivity" refers to the quantity of a fatty amine or fatty amine related compound including a composition or blend of one or more fatty amines produced per unit volume of host cell culture per unit time. In any aspect of the compositions and methods described herein, the productivity of a fatty amine related compound including a composition or blend of fatty amines produced by a recombinant host cell is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, 2500 mg/L/hour, or as high as 10 g/L/hour (dependent upon cell mass). For example, the productivity of a fatty amine related compound including a composition or blend of fatty amines produced by a recombinant host cell according to the methods of the present disclosure may be from 500 mg/L/hour to 2500 mg/L/hour, or from 700 mg/L/hour to 2000 mg/L/hour. The productivity may refer to a particular fatty amine related compound including a composition of fatty amines or a blend of fatty amine or a combination of fatty amines produced by a given host cell culture. For example, the expression of a biosynthetic protein that can convert a fatty aldehyde to a fatty amine in a recombinant host cell such as *E. coli* results in the production of an increased productivity of fatty amine derived compounds including fatty amines and compositions and blends thereof as compared to a recombinant host cell expressing the corresponding wild type polypeptide. In one embodiment, the higher productivity ranges from about 0.3 g/L/h to about 3 g/L/h.

As used herein, the term "total fatty species" and "total fatty amine product" and "fatty amine derivative" may be used interchangeably herein with reference to the amount of fatty amines that can be produced by the host cell that expresses the biosynthetic protein that can convert a fatty aldehyde to a fatty amine, as evaluated by GC-FID.

As used herein, the term "glucose utilization rate" means the amount of glucose used by the culture per unit time, reported as grams/liter/hour (g/L/hr).

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. The carbon source can also be a product of photosynthesis, such as glucose. In certain embodiments, the carbon source is gas mixture containing CO coming from flu gas. In another embodiment, the carbon source is a gas mixture containing CO coming from the reformation of a carbon containing material, such as biomass, coal, or natural gas. In other embodiments the carbon source is syngas, methane, or natural gas. In certain preferred embodiments, the carbon source is biomass. In other preferred embodiments, the carbon source is glucose. In other preferred embodiments the carbon source is sucrose. In other embodiments the carbon source is glycerol. In other preferred embodiments the carbon source is sugar can juice, sugar cane syrup, or corn syrup. In other preferred embodiments, the carbon source is derived from renewable feedstocks, such as $CO_2$, CO, glucose, sucrose, xylose, arabinose, glycerol, mannose, or mixtures thereof. In other embodiments, the carbon source is derived from renewable feedstocks including starches, cellulosic biomass, molasses, and other sources of carbohydrates including carbohydrate mixtures derived from hydrolysis of cellulosic biomass, or the waste materials derived from plant- or natural oil processing.

As used herein, the term "biomass" refers to any biological material from which a carbon source is derived. In some embodiments, a biomass is processed into a carbon source, which is suitable for bioconversion. In other embodiments, the biomass does not require further processing into a carbon source. The carbon source can be converted into a composition comprising fatty amines. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, glycerol, fermentation waste, ensilage, straw, lumber, sewage, garbage, cellulosic urban waste, and food leftovers (e.g., soaps, oils and fatty acids). The term "biomass" can also refer to sources of carbon, such as carbohydrates (e.g., monosaccharides, disaccharides, or polysaccharides).

As used herein, the term "isolated," with respect to products (such as fatty amines and compositions and blends thereof) refers to products that are separated from cellular components, cell culture media, or chemical or synthetic precursors. The fatty amines produced by the methods described herein can be relatively immiscible in the fermentation broth, as well as in the cytoplasm. Therefore, the fatty amines can collect in an organic phase either intracellularly or extracellularly.

As used herein, the terms "purify," "purified," or "purification" mean the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, and at least about 99% free) from other components with which they are associated. As used herein, these terms also refer to the removal of contaminants from a sample. For example, the removal of contaminants can result in an increase in the percentage of fatty amine derived compounds including fatty amines and compositions and blends thereof in a sample. For example, when a fatty amine related compound is produced in a recombinant host cell, the fatty amine related compound can be purified by the removal of host cell proteins and/or other host cell material. After purification, the percentage of fatty amines in the sample is increased. The terms "purify," "purified," and "purification" are relative terms which do not require absolute purity. Thus, for example, when a fatty amine related compound is produced in recombinant host cells, the fatty amine compound is substantially separated from other cellular components (e.g., nucleic acids, polypeptides, lipids, carbohydrates, or other hydrocarbons).

As used herein, the term "attenuate" means to weaken, reduce, or diminish. For example, a polypeptide can be attenuated by modifying the polypeptide to reduce its activity (e.g., by modifying a nucleotide sequence that encodes the polypeptide).

The term "fatty aldehyde producing biosynthetic enzyme" or "fatty aldehyde generating enzyme" are used interchangeably herein and refer to a polypeptide or a protein or an enzyme that has the enzymatic activity to generate fatty aldehydes or fatty aldehyde precursors. Examples of such enzymes include, but are not limited to, a carboxylic acid reductase (CAR) (e.g., CarB) and/or a thioesterase (TE) (e.g., TesA, 'tesA); an acyl-ACP reductase (AAR) (e.g., from *Synechococcus elongatus* PCC7942); an acyl-CoA reductase (e.g., Acr1); a phosphopanthetheinyl transferase (PPTase); and the like.

From Fatty Aldehyde Precursors to Fatty Amines

The disclosure relates to microbial production of fatty amines. As shown herein, microorganisms can be genetically engineered to express various biosynthetic enzymes in order to produce fatty amines in vivo. More specifically, a microorganism can be genetically engineered to express a metabolic pathway that converts a fatty aldehyde to a fatty amine. The pathway expresses at least one biosynthetic enzyme that has aminotransferase (e.g., putrescine aminotransferase (YgjG) or GABA aminotransferase (PuuE) from *Escherichia coli*) or amine dehydrogenase (e.g., methylamine dehydrogenase of *Paracoccus denitrificans* or quinohemo protein amine dehydrogenase of *Pseudomonas* spp.) or amine oxidase activity to convert fatty aldehydes to fatty amines. Transaminases carry out the same reaction as aminotransferases and these names are sometimes used interchangeably. For example, GABA aminotransferase is also referred to as 4-aminobutyrate transaminase. In one embodiment, the aminotransferase or transaminase or amine dehydrogenase or amine oxidase is an exogenous biosynthetic enzyme or exogenously expressed in the cell. Alternatively, the fatty amines can be produced by combining the engineered pathways for fatty amine production expressing a biosynthetic enzyme that has aminotransferase or amine dehydrogenase or amine oxidase activity to convert fatty aldehydes to fatty amines with an engineered pathway for fatty aldehyde production expressing an exogenous biosynthetic enzyme that produces fatty aldehydes. Such fatty aldehyde precursors can be generated in vivo through a variety of processes and engineered pathways, such as an engineered carboxylic acid reductase (CAR) pathway utilized for fatty aldehyde production (see U.S. Pat. No. 8,097,439, incorporated herein by reference) or an engineered CAR and thioesterase (TE) pathway utilized for fatty alcohol production (see U.S. Pat. No. 8,097,439, supra) or an engineered phosphopanthetheinyl transferase (PPTase) and CAR pathway utilized for fatty aldehyde or fatty alcohol production (see U.S. Application Publication No. 20130035513, incorporated herein by reference) or an engineered acyl-ACP reductase (AAR) pathway utilized for fatty aldehyde production (see U.S. Pat. No. 8,268,599, incorporated herein by reference) or for alkane production (see U.S.

Pat. No. 8,323,924, incorporated herein by reference). An example of a suitable TE is 'TesA (i.e., a truncated thioesterase from *E. coli* that has its periplasm leader sequence removed (hence the apostrophe), such that it remains in the cytoplasm); an example of a suitable CAR is CarB; an example of a suitable AAR is the enzyme from *Synechococcus elongatus* PCC7942 (see Table 6, infra).

In one embodiment, co-expression of an engineered pathway for fatty aldehyde production and an engineered pathway for fatty amine production with the expression of an biosynthetic enzyme having aminotransferase or amine dehydrogenase or amine oxidase activity, along with supplementation with an appropriate nitrogen source (e.g., glutamate or ammonia or hydrogen peroxide) allows for the conversion of an aldehyde precursor into the corresponding amine (see Table 1 for putrescine aminotransferase; see Tables 2, 3 and 4 for examples of enzymatic reactions). The availability of nitrogen donors (e.g., glutamate) for the aminotransferase reaction can be optionally enhanced by overexpress sing glutamate dehydrogenase to increase the rate of glutamate biosynthesis. The native *E. coli* glutamate dehydrogenase uses NADPH as a redox cofactor, thus, replacing this enzyme with a glutamate dehydrogenase that is capable of using NADH instead (such as, for example, the glutamate dehydrogenases from *Bacteroides* spp. including, but not limited to, *B. thetaiotaomicron, B. fragilis, B. distasonis, B. ovatus, B. vulgatus*, and *B. Uniformis*) can increase the availability of NADPH in the cell. This can provide an increased supply of NADPH for other biosynthetic processes that depend on NADPH (e.g., fatty acid biosynthesis).

Table 1 below (infra) depicts EC numbers and names for various biosynthetic enzymes that are useful in the production of amines including aminotransferases/transaminases. The enzyme commission or classification number (EC number) is a numerical classification scheme for enzymes, based on the chemical reactions they catalyze. The EC numbers do not technically specify enzymes, rather they specify enzyme-catalyzed reactions. For example, if different enzymes (e.g., from different organisms) catalyze the same reaction, then they receive the same EC number. In addition, different protein folds can catalyze an identical reaction and can therefore be assigned an identical EC number because of convergent evolution (i.e., these are called non-homologous isofunctional enzymes, or NISE). As shown in Table 1, the enzymatic activity of putrescine aminotransferase is classified under EC number 2.6.1.82. All the enzymes shown in Table 1 participate in chemical reactions that result in amines and are classified as aminotransferases/transaminases because their EC number falls under EC 2.6.1 (see also Table 7, infra). Table 2 below (infra) shows a number of different biosynthetic enzymes that can produce fatty amines from fatty aldehyde precursors. For example, aminotransferases or transaminases, amine oxidases and amine dehydrogenases catalyze reactions where fatty aldehyde precursors are converted to fatty amines. In one embodiment, an engineered metabolic pathway includes an aminotransferase or transaminase for production of fatty aldehydes in vivo. In another embodiment, an engineered metabolic pathway includes an amine oxidase for production of fatty aldehydes in vivo. In another embodiment, an engineered metabolic pathway includes an amine dehydrogenase for production of fatty aldehydes in vivo. Table 3 below (infra) shows the reaction catalyzed by putrescine aminotransferase, i.e., converting fatty aldehydes to fatty amines.

TABLE 1

Enzymes Involved in the Production of Amines under EC 2.6.1

| | |
|---|---|
| 2.6.1.1 | Aspartate transaminase. |
| 2.6.1.2 | Alanine transaminase. |
| 2.6.1.3 | Cysteine transaminase. |
| 2.6.1.4 | Glycine transaminase. |
| 2.6.1.5 | Tyrosine transaminase. |
| 2.6.1.6 | Leucine transaminase. |
| 2.6.1.7 | Kynurenine-oxoglutarate transaminase. |
| 2.6.1.8 | 2,5-diaminovalerate transaminase. |
| 2.6.1.9 | Histidinol-phosphate transaminase. |
| 2.6.1.10 | Transferred entry: 2.6.1.21. |
| 2.6.1.11 | Acetylornithine transaminase. |
| 2.6.1.12 | Alanine-oxo-acid transaminase. |
| 2.6.1.13 | Ornithine aminotransferase. |
| 2.6.1.14 | Asparagine-oxo-acid transaminase. |
| 2.6.1.15 | Glutamine-pyruvate transaminase. |
| 2.6.1.16 | Glutamine-fructose-6-phosphate transaminase (isomerizing). |
| 2.6.1.17 | Succinyldiaminopimelate transaminase. |
| 2.6.1.18 | Beta-alanine-pyruvate transaminase. |
| 2.6.1.19 | 4-aminobutyrate transaminase. |
| 2.6.1.20 | Deleted entry. |
| 2.6.1.21 | D-amino-acid transaminase. |
| 2.6.1.22 | (S)-3-amino-2-methylpropionate transaminase. |
| 2.6.1.23 | 4-hydroxyglutamate transaminase. |
| 2.6.1.24 | Diiodotyrosine transaminase. |
| 2.6.1.25 | Transferred entry: 2.6.1.24. |
| 2.6.1.26 | Thyroid-hormone transaminase. |
| 2.6.1.27 | Tryptophan transaminase. |
| 2.6.1.28 | Tryptophan-phenylpyruvate transaminase. |
| 2.6.1.29 | Diamine transaminase. |
| 2.6.1.30 | Pyridoxamine-pyruvate transaminase. |
| 2.6.1.31 | Pyridoxamine-oxaloacetate transaminase. |
| 2.6.1.32 | Valine-3-methyl-2-oxovalerate transaminase. |
| 2.6.1.33 | dTDP-4-amino-4,6-dideoxy-D-glucose transaminase. |
| 2.6.1.34 | UDP-2-acetamido-4-amino-2,4,6-trideoxyglucose transaminase. |
| 2.6.1.35 | Glycine-oxaloacetate transaminase. |
| 2.6.1.36 | L-lysine 6-transaminase. |
| 2.6.1.37 | 2-aminoethylphosphonate-pyruvate transaminase. |
| 2.6.1.38 | Histidine transaminase. |
| 2.6.1.39 | 2-aminoadipate transaminase. |
| 2.6.1.40 | (R)-3-amino-2-methylpropionate-pyruvate transaminase. |
| 2.6.1.41 | D-methionine-pyruvate transaminase. |
| 2.6.1.42 | Branched-chain-amino-acid transaminase. |
| 2.6.1.43 | Aminolevulinate transaminase. |
| 2.6.1.44 | Alanine-glyoxylate transaminase. |
| 2.6.1.45 | Serine-glyoxylate transaminase. |
| 2.6.1.46 | Diaminobutyrate-pyruvate transaminase. |
| 2.6.1.47 | Alanine-oxomalonate transaminase. |
| 2.6.1.48 | 5-aminovalerate transaminase. |
| 2.6.1.49 | Dihydroxyphenylalanine transaminase. |
| 2.6.1.50 | Glutamine-scyllo-inositol transaminase. |
| 2.6.1.51 | Serine-pyruvate transaminase. |
| 2.6.1.52 | Phosphoserine transaminase. |
| 2.6.1.53 | Transferred entry: 1.4.1.13. |
| 2.6.1.54 | Pyridoxamine-phosphate transaminase. |
| 2.6.1.55 | Taurine-2-oxoglutarate transaminase. |
| 2.6.1.56 | 1D-1-guanidino-3-amino-1,3-dideoxy-scyllo-inositol transaminase. |
| 2.6.1.57 | Aromatic-amino-acid transaminase. |
| 2.6.1.58 | Phenylalanine(histidine)transaminase. |
| 2.6.1.59 | dTDP-4-amino-4,6-dideoxygalactose transaminase. |
| 2.6.1.60 | Aromatic-amino-acid-glyoxylate transaminase. |
| 2.6.1.61 | Deleted entry. |
| 2.6.1.62 | Adenosylmethionine-8-amino-7-oxononanoate transaminase. |
| 2.6.1.63 | Kynurenine-glyoxylate transaminase. |
| 2.6.1.64 | Glutamine-phenylpyruvate transaminase. |
| 2.6.1.65 | N(6)-acetyl-beta-lysine transaminase. |
| 2.6.1.66 | Valine-pyruvate transaminase. |
| 2.6.1.67 | 2-aminohexanoate transaminase. |
| 2.6.1.68 | Ornithine(lysine)transaminase. |
| 2.6.1.69 | Deleted entry. |
| 2.6.1.70 | Aspartate-phenylpyruvate transaminase. |
| 2.6.1.71 | Lysine-pyruvate 6-transaminase. |
| 2.6.1.72 | D-4-hydroxyphenylglycine transaminase. |
| 2.6.1.73 | Methionine-glyoxylate transaminase. |
| 2.6.1.74 | Cephalosporin-C-transaminase. |
| 2.6.1.75 | Cysteine-conjugate transaminase. |
| 2.6.1.76 | Diaminobutyrate-2-oxoglutarate transaminase. |
| 2.6.1.77 | Taurine-pyruvate aminotransferase. |

TABLE 1-continued

Enzymes Involved in the Production of Amines under EC 2.6.1

| | |
|---|---|
| 2.6.1.78 | Aspartate-prephenate aminotransferase. |
| 2.6.1.79 | Glutamate-prephenate aminotransferase. |
| 2.6.1.80 | Nicotianamine aminotransferase. |
| 2.6.1.81 | Succinylornithine transaminase. |
| 2.6.1.82 | Putrescine aminotransferase. |
| 2.6.1.83 | LL-diaminopimelate aminotransferase. |
| 2.6.1.84 | Arginine-pyruvate transaminase. |
| 2.6.1.85 | Aminodeoxychorismate synthase. |
| 2.6.1.86 | 2-amino-4-deoxychorismate synthase. |

TABLE 2

Enzymatic Reactions that Produce Fatty Amines
Fatty Amine Production from Fatty Aldehydes

| Enzymes | Reactions |
|---|---|
| Aminotransferase/transaminase | $R_1\text{-CHO} + R_2\text{-CHO} \rightleftharpoons R_1\text{-CH}_2\text{-NH}_2 + R_2\text{-CHO}$ |
| Amine oxidase | $R\text{-CHO} + NH_3 + H_2O_2 \rightleftharpoons O_2 + H_2O + R\text{-CH}_2\text{-NH}_2$ |
| Amine dehydrogenase | $R\text{-CHO} + NH_3 + TTQ_{OX} \rightleftharpoons TTQ_{re} + H_2O + R\text{-CH}_2\text{-NH}_2$ |

TABLE 3

Enzymatic Reaction of Putrescine Aminotransferase
Putrescine Aminotransferase Enzymatic Reaction $H_2N\text{-}(CH_2)_4\text{-}NH_2$ + 2-oxoglutarate $\rightleftharpoons$ $H_2N\text{-}(CH_2)_3\text{-}CHO$ + glutamate In order to illustrate the disclosure, recombinant host cells were engineered to express a thioesterase (TE), which catalyzes the conversion of acyl-ACPs or acyl-CoAs into free fatty acids; and a carboxylic acid reductase (CAR), which converts the free fatty acids into fatty aldehydes. The recombinant host cells were further engineered to express a putrescine aminotransferase (YgjG) in order to convert the fatty aldehydes to fatty amines (see Example 1 for experimental results; see Table 3 (supra) for the enzymatic reaction carried out by YgjG; see Table 5 (infra) for the aminotransferase/transaminase mechanism). Herein, the ygjG gene was cloned from *E. coli* and ligated into an expression vector to generate an expression plasmid. A second expression plasmid was generated by cloning and integrating a carB and a tesA gene. Cells were then transformed with both plasmids and cultured in a fermentation broth with a carbon source. The production of fatty amines was confirmed while control cells did not produce fatty amines (see Example 1). Any suitable aminotransferase/transaminase can be used to produce fatty amines so long as the enzymatic activity can convert fatty aldehydes into fatty amines. If the cell naturally produces fatty aldehydes then the cell is engineered to express an exogenous putrescine aminotransferase (YgjG) as shown in Example 1 in order to convert the naturally present fatty aldehydes to fatty amines.

In another embodiment, an amine dehydrogenase can be used instead of an aminotransferase to convert fatty aldehydes into fatty amines (see Table 4 (infra) for the enzymatic reaction carried out by an amine dehydrogenase; and Table 7 (infra) for examples of enzymes). This is applicable if the nitrogen source is ammonia rather than amino acids. Examples of amine dehydrogenases are useful to convert fatty aldehydes to fatty amines fall under EC numbers EC 1.4.9; EC 1.4.98; and EC 1.4.99 (see Table 7, infra). For example, alanine dehydrogenase, glutamate dehydrogenase, L-lysine-6-dehydrogenase; and methylamine dehydrogenase are examples of amine dehydrogenases that can be used to convert fatty aldehydes into fatty amines (see Table 7, infra).

In yet another embodiment, amine oxidase can be used instead of an aminotransferase to convert fatty aldehydes into fatty amines.

TABLE 4

Amine Dehydrogenase Reaction
Amine Dehydrogenase Enzymatic Reaction

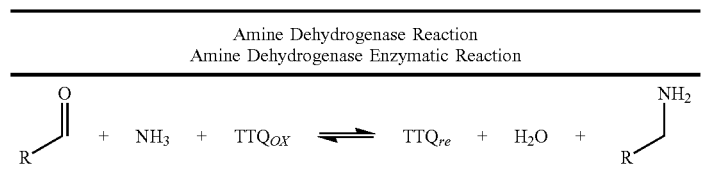

TABLE 5

Mechanism for Aminotransferase/Transaminase
Aminotransferase Mechanism

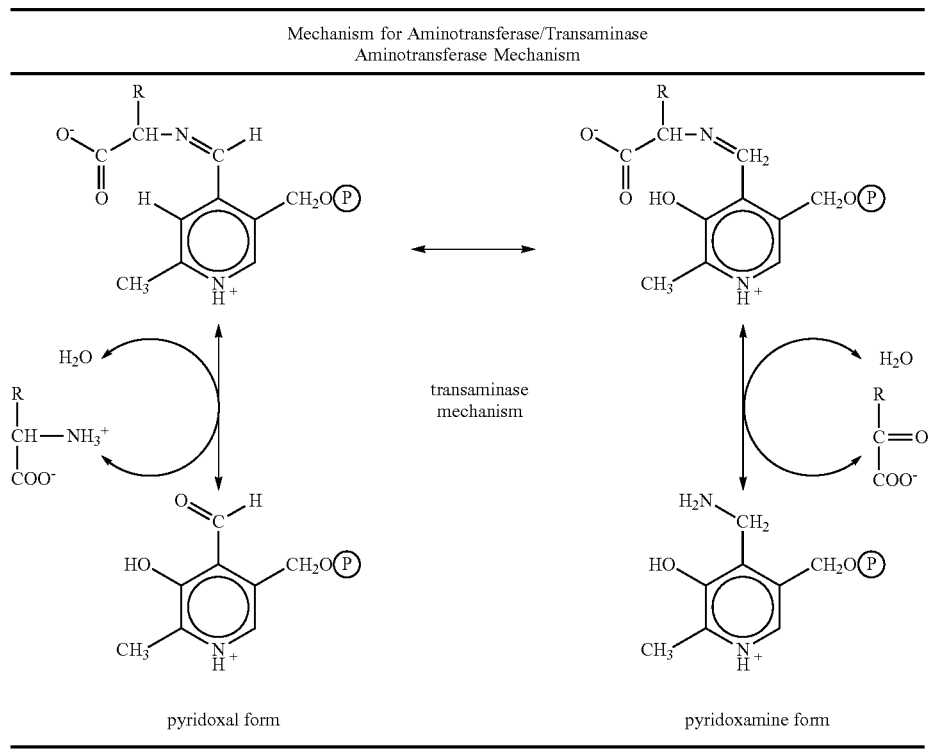

Tables 6 and 7 below (infra) depict various enzymatic activities and their corresponding enzyme classification (EC) numbers.

TABLE 6

Enzymatic Activities

| Gene Designation | Source Organism | Enzyme Name | Accession # | EC Number | Exemplary Use |
|---|---|---|---|---|---|
| | | Fatty Acid Production Increase | | | |
| accA | E. coli, Lactococci | Acetyl-CoA carboxylase, subunit A (carboxyltransferase alpha) | AAC73296, NP_414727 | 6.4.1.2 | increase Malonyl-CoA production |
| accB | E. coli, Lactococci | Acetyl-CoA carboxylase, subunit B (BCCP: biotin carboxyl carrier protein) | NP_417721 | 6.4.1.2 | increase Malonyl-CoA production |

TABLE 6-continued

Enzymatic Activities

| Gene Designation | Source Organism | Enzyme Name | Accession # | EC Number | Exemplary Use |
|---|---|---|---|---|---|
| accC | E. coli, Lactococci | Acetyl-CoA carboxylase, subunit C (biotin carboxylase) | NP_417722 | 6.4.1.2, 6.3.4.14 | increase Malonyl-CoA production |
| accD | E. coli, Lactococci | Acetyl-CoA carboxylase, subunit D (carboxyltransferase beta) | NP_416819 | 6.4.1.2 | increase Malonyl-CoA production |
| fadD | E. coli W3110 | acyl-CoA synthase | AP_002424 | 2.3.1.86, 6.2.1.3 | increase Fatty acid production |
| fabA | E. coli K12 | β-hydroxydecanoyl thioester dehydratase/isomerase | NP_415474 | 4.2.1.60 | increase fatty acyl-ACP/CoA production |
| fabB | E. coli | 3-oxoacyl-[acyl-carrier-protein] synthase I | BAA16180 | 2.3.1.41 | increase fatty acyl-ACP/CoA production |
| fabD | E. coli K12 | [acyl-carrier-protein] S-malonyltransferase | AAC74176 | 2.3.1.39 | increase fatty acyl-ACP/CoA production |
| fabF | E. coli K12 | 3-oxoacyl-[acyl-carrier-protein] synthase II | AAC74179 | 2.3.1.179 | increase fatty acyl-ACP/CoA production |
| fabG | E. coli K12 | 3-oxoacyl-[acyl-carrier protein] reductase | AAC74177 | 1.1.1.100 | increase fatty acyl-ACP/CoA production |
| fabH | E. coli K12 | 3-oxoacyl-[acyl-carrier-protein] synthase III | AAC74175 | 2.3.1.180 | increase fatty acyl-ACP/CoA production |
| fabI | E. coli K12 | enoyl-[acyl-carrier-protein] reductase | NP_415804 | 1.3.1.9 | increase fatty acyl-ACP/CoA production |
| fabR | E. coli K12 | Transcriptional Repressor | NP_418398 | none | modulate unsaturated fatty acid production |
| fabV | Vibrio cholerae | enoyl-[acyl-carrier-protein] reductase | YP_001217283 | 1.3.1.9 | increase fatty acyl-ACP/CoA production |
| fabZ | E. coli K12 | (3R)-hydroxymyristol acyl carrier protein dehydratase | NP_414722 | 4.2.1.- | increase fatty acyl-ACP/CoA production |
| fadE | E. coli K13 | acyl-CoA dehydrogenase | AAC73325 | 1.3.99.3, 1.3.99.- | reduce fatty acid degradation |
| fadD | E. coli K12 | acyl-CoA synthetase | NP_416319 | 6.2.1.3 | reduce fatty acid degradation |
| fadA | E. coli K12 | 3-ketoacyl-CoA thiolase | YP_02627 | 2.3.1.16 | reduce fatty acid degradation |
| fadB | E. coli K12 | enoyl-CoA hydratase, 3-OH acyl-CoA epimerase/ dehydrogenase | NP_418288 | 4.2.1.17, 5.1.2.3, 1.1.1.35 | reduce fatty acid degradation |
| fadR | E. coli | transcriptional regulatory protein | NP_415705 | none | Block or reverse fatty acid degradation |

Chain Length Control

| | | | | | |
|---|---|---|---|---|---|
| tesA (with or without leader sequence) | E. coli | thioesterase - leader sequence is amino acids 1-26 | P0ADA1 | 3.1.2.-, 3.1.1.5 | C18 Chain Length |
| tesA (without leader sequence) | E. coli | thioesterase | AAC73596, NP_415027 | 3.1.2.-, 3.1.1.5 | C18:1 Chain Length |
| tesA (mutant of E. coli thioesterase I complexed with octanoic acid) | E. coli | thioesterase | L109P | 3.1.2.-, 3.1.1.5 | <C18 Chain Length |
| fatB1 | Umbellularia californica | thioesterase | Q41635 | 3.1.2.14 | C12:0 Chain Length |
| fatB2 | Cuphea hookeriana | thioesterase | AAC49269 | 3.1.2.14 | C8:0-C10:0 Chain Length |
| fatB3 | Cuphea hookeriana | thioesterase | AAC72881 | 3.1.2.14 | C14:0-C16:0 Chain Length |
| fatB | Cinnamomumcamphora | thioesterase | Q39473 | 3.1.2.14 | C14:0 Chain Length |
| fatB | Arabidopsis thaliana | thioesterase | CAA85388 | 3.1.2.14 | C16:1 Chain Length |
| fatB1 | Umbellularia californica | thioesterase | Q41635 | 3.1.2.14 | C12:0 Chain Length |
| fatA1 | Helianthus annuus | thioesterase | AAL79361 | 3.1.2.14 | C18:1 Chain Length |

TABLE 6-continued

Enzymatic Activities

| Gene Designation | Source Organism | Enzyme Name | Accession # | EC Number | Exemplary Use |
|---|---|---|---|---|---|
| fatA | Arabidopsis thaliana | thioesterase | NP_189147, NP_193041 | 3.1.2.14 | C18:1 Chain Length |
| fatA | Brassica juncea | thioesterase | CAC39106 | 3.1.2.14 | C18:1 Chain Length |
| fatA | Cuphea hookeriana | thioesterase | AAC72883 | 3.1.2.14 | C18:1 Chain Length |
| tes | Photbacterium profundum | thioesterase | YP_130990 | 3.1.2.14 | Chain Length |
| tesB | E. coli | thioesterase | NP_414986 | 3.1.2.14 | Chain Length |
| fadM | E. coli | thioesterase | NP_414977 | 3.1.2.14 | Chain Length |
| yciA | E. coli | thioesterase | NP_415769 | 3.1.2.14 | Chain Length |
| ybgC | E. coli | thioesterase | NP_415264 | 3.1.2.14 | Chain Length |
| Saturation Level Control | | | | | |
| Sfa | E. coli | Suppressor of fabA | AAN79592, AAC44390 | none | increase mono-unsaturated fatty acids |
| fabA | E. coli K12 | β-hydroxydecanoyl thioester dehydratase/isomerase | NP_415474 | 4.2.1.60 | produce unsaturated fatty acids |
| GnsA | E. coli | suppressors of the secG null mutation | ABD18647.1 | none | increase unsaturated fatty acid esters |
| GnsB | E. coli | suppressors of the secG null mutation | AAC74076.1 | none | increase unsaturated fatty acid esters |
| fabB | E. coli | 3-oxoacyl-[acyl-carrier-protein] synthase I | BAA16180 | 2.3.1.41 | modulate unsaturated fatty acid production |
| des | Bacillus subtilis | D5 fatty acyl desaturase | O34653 | 1.14.19 | modulate unsaturated fatty acid production |
| Ester Production | | | | | |
| AT3G51970 | Arabidopsis thaliana | long-chain-alcohol O-fatty-acyltransferase | NP_190765 | 2.3.1.26 | ester production |
| ELO1 | Pichia angusta | Fatty acid elongase | BAD98251 | 2.3.1.- | produce very long chain length fatty acids |
| plsC | Saccharomyces cerevisiae | acyltransferase | AAA16514 | 2.3.1.51 | ester production |
| DAGAT/DGAT | Arabidopsis thaliana | diacylglycerol acyltransferase | AAF19262 | 2.3.1.20 | ester production |
| hWS | Homo sapiens | acyl-CoA wax alcohol acyltransferase | AAX48018 | 2.3.1.20 | ester production |
| aft1 | Acinetobacter sp. ADP1 | bifunctional wax ester synthase/acyl-CoA: diacylglycerol acyltransferase | AAO17391 | 2.3.1.20 | ester production |
| ES9 | Marinobacter hydrocarbonoclasticus | wax ester synthase | ABO21021 | 2.3.1.20 | ester production |
| mWS | Simmondsia chinensis | wax ester synthase | AAD38041 | 2.3.1.- | ester production |
| Fatty Alcohol Output | | | | | |
| | | thioesterases (see above) | | | increase fatty acid/fatty alcohol production |
| BmFAR | Bombyxmori | FAR (fatty alcohol forming acyl-CoA reductase) | BAC79425 | 1.1.1.- | convert acyl-CoA to fatty alcohol |
| acr1 | Acinetobacter sp. ADP1 | acyl-CoA reductase | YP_047869 | 1.2.1.42 | reduce fatty acyl-CoA to fatty aldehydes |
| yqhD | E. coli W3110 | alcohol dehydrogenase | AP_003562 | 1.1.-.- | reduce fatty aldehydes to fatty alcohols; increase fatty alcohol production |
| alrA | Acinetobacter sp. ADP1 | alcohol dehydrogenase | CAG70252 | 1.1.-.- | reduce fatty aldehydes to fatty alcohols |
| BmFAR | Bombyxmori | FAR (fatty alcohol forming acyl-CoA reductase) | BAC79425 | 1.1.1.- | reduce fatty acyl-CoA to fatty alcohol |
| GTNG_1865 | Geobacillusthermo-denitrificans NG80-2 | Long-chain aldehyde dehydrogenase | YP_001125970 | 1.2.1.3 | reduce fatty aldehydes to fatty alcohols |
| AAR | Synechococcus elongatus | Acyl-ACP reductase | YP_400611 | 1.2.1.42 | reduce fatty acyl-ACP/CoA to fatty aldehydes |
| carB | Mycobacterium smegmatis | carboxylic acid reductase protein | YP_889972 | 6.2.1.3, 1.2.1.42 | reduce fatty acids to fatty aldehyde |
| FadD | E. coli K12 | acyl-CoA synthetase | NP_416319 | 6.2.1.3 | activates fatty acids to fatty acyl-CoAs |

TABLE 6-continued

Enzymatic Activities

| Gene Designation | Source Organism | Enzyme Name | Accession # | EC Number | Exemplary Use |
|---|---|---|---|---|---|
| atoB | Erwiniacarotovora | acetyl-CoA acetyltransferase | YP_049388 | 2.3.1.9 | production of butanol |
| hbd | Butyrivibriofibrisolvens | Beta-hydroxybutyryl-CoA dehydrogenase | BAD51424 | 1.1.1.157 | production of butanol |
| CPE0095 | Clostridium perfringens | crotonasebutyryl-CoA dehydryogenase | BAB79801 | 4.2.1.55 | production of butanol |
| bcd | Clostridium beijerinckii | butyryl-CoA dehydryogenase | AAM14583 | 1.3.99.2 | production of butanol |
| ALDH | Clostridium beijerinckii | coenzyme A-acylating aldehyde dehydrogenase | AAT66436 | 1.2.1.3 | production of butanol |
| AdhE | E. coli CFT073 | aldehyde-alcohol dehydrogenase | AAN80172 | 1.1.1.1 1.2.1.10 | production of butanol |

Fatty Alcohol Acetyl Ester Output

| | | thioesterases (see above) | | | modify output |
|---|---|---|---|---|---|
| acr1 | Acinetobacter sp. ADP1 | acyl-CoA reductase | YP_047869 | 1.2.1.42 | modify output |
| yqhD | E. Coli K12 | alcohol dehydrogenase | AP_003562 | 1.1.-.- | modify output |
| AAT | Fragaria x ananassa | alcohol O-acetyltransferase | AAG13130 | 2.3.1.84 | modify output |

Terminal Olefin Output

| OleT | Jeotgalicoccus sp. | Fatty acid decarboxylase | HQ709266 | 1.11.2.4 | decarboxylate fatty acids |
|---|---|---|---|---|---|

Product Export

| AtMRP5 | Arabidopsis thaliana | Arabidopsis thaliana multidrug resistance-associated | NP_171908 | none | modify product export amount |
|---|---|---|---|---|---|
| AmiS2 | Rhodococcus sp. | ABC transporter AmiS2 | JC5491 | none | modify product export amount |
| AtPGP1 | Arabidopsis thaliana | Arabidopsis thaliana p glycoprotein 1 | NP_181228 | none | modify product export amount |
| AcrA | CandidatusProtochlamydiaamoebophila UWE25 | putative multidrug-efflux transport protein acrA | CAF23274 | none | modify product export amount |
| AcrB | CandidatusProtochlamydiaamoebophila UWE25 | probable multidrug-efflux transport protein, acrB | CAF23275 | none | modify product export amount |
| TolC | Francisellatularensis subsp. novicida | Outer membrane protein [Cell envelope biogenesis, | ABD59001 | none | modify product export amount |
| AcrE | Shigellasonnei Ss046 | transmembrane protein affects septum formation and cell membrane permeability | YP_312213 | none | modify product export amount |
| AcrF | E. coli | Acriflavine resistance protein F | P24181 | none | modify product export amount |
| tll1619 | Thermosynechococcus elongatus [BP-1] | multidrug efflux transporter | NP_682409.1 | none | modify product export amount |
| tll0139 | Thermosynechococcus elongatus [BP-1] | multidrug efflux transporter | NP_680930.1 | none | modify product export amount |

Fermentation

| replication checkpoint genes | | | | | increase output efficiency |
|---|---|---|---|---|---|
| umuD | Shigellasonnei Ss046 | DNA polymerase V, subunit | YP_310132 | 3.4.21.- | increase output efficiency |
| umuC | E. coli | DNA polymerase V, subunit | ABC42261 | 2.7.7.7 | increase output efficiency |
| pntA, pntB | Shigellaflexneri | NADH: NADPH transhydrogenase (alpha and beta subunits) | P07001, P0AB70 | 1.6.1.2 | increase output efficiency |

Other

| fabK | Streptococcus pneumoniae | trans-2-enoyl-ACP reductase II | AAF98273 | 1.3.1.9 | Contributes to fatty acid biosynthesis |
|---|---|---|---|---|---|

TABLE 6-continued

Enzymatic Activities

| Gene Designation | Source Organism | Enzyme Name | Accession # | EC Number | Exemplary Use |
|---|---|---|---|---|---|
| fabL | *Bacillus licheniformis* DSM 13 | enoyl-(acyl carrier protein) reductase | AAU39821 | 1.3.1.9 | Contributes to fatty acid biosynthesis |
| fabM | *Streptococcus mutans* | trans-2, cis-3-decenoyl-ACP isomerase | DAA05501 | 4.2.1.17 | Contributes to fatty acid biosynthesis |

TABLE 7

Examples of Amino Transferases/Transaminases (EC 2.6.1) and Amine Dehydrogenases (EC 1.4.9, EC 1.4.98, EC 1.4.99)

| Designation/Name | Function | Organism | Accession # |
|---|---|---|---|
| Beta alanine-pyruvate transaminase | Beta-alanine: pyruvate transaminase | *Pseudomonas aeruginosa* PA7 | YP_001345604 |
| ygjG | Putrescine aminotransferase | *Escherichia coli* MG1655 | NP_417544 |
| gabT | 5-aminovalerate transaminase | *Pseudomonas aeruginosa* PA01 | AAG03655 |
| Lat | L-lysine 6-transaminase | *Mycobacterium tuberculosis* H37Rv | NP_217807 |
| GABA-T | 4-aminobutyrate transaminase | *Sus scrofa* | NP_999428 |
| Ald | Alanine dehydrogenase | *Bacillus subtilis* subsp. *natto* BEST195 | BAI86717 |
| gdhA | Glutamate dehydrogenase (NADPH) | *Escherichia coli* MG1655 | NP_416275 |
| Gdh | Glutamate dehydrogenase (NADH) | *Peptoniphilus asaccharolyticus* | AAA25611 |
| L-lysine 6-dehydrogenase | L-lysine 6-dehydrogenase | *Achromobacter denitrificans* | AAZ94428 |
| mauRFBEDACJGMN | Methylamine dehydrogenase | *Paracoccus denitrificans* | P52685.1<br>P29897.2<br>P29894.1<br>P29896.2<br>P29895.2<br>P22619.2<br>P22364.1<br>P22566.2<br>ABL72797.1<br>ABL72798.1<br>AAA86469.1 |

Microbial Host Cells and their Cultures

The microorganisms of the disclosure function as microbial host cells and encompass one or more polynucleotide sequences that include an open reading frame encoding at least one exogenous biosynthetic enzyme of the present disclosure. In one embodiment, a fatty amine composition is produced by culturing host cells that express an exogenous biosynthetic enzyme (e.g., aminotransferases/transaminases or amine dehydrogenases or amine oxidases) in the presence of a carbon source under conditions effective to express the fatty amines. In another embodiment, a fatty amine composition is produced by culturing host cells that express one or more of an exogenous biosynthetic enzyme (e.g., aminotransferases/transaminases or amine dehydrogenases or amine oxidases in combination with one or more aldehyde generating enzymes such as a CAR (e.g., CarB) and/or a TE (e.g., TesA, 'tesA) in the presence of a carbon source under conditions effective to express the fatty amines. In another embodiment, a fatty amine composition is produced by culturing host cells that express one or more of an exogenous biosynthetic enzyme (e.g., aminotransferases/transaminases or amine dehydrogenases or amine oxidases in combination with one or more aldehyde generating enzymes such as an acyl-ACP reductase (AAR) (e.g., from *Synechococcus elongatus* PCC7942) in the presence of a carbon source under conditions effective to express the fatty amines. In another embodiment, a fatty amine composition is produced by culturing host cells that express one or more of an exogenous biosynthetic enzyme (e.g., aminotransferases/transaminases or amine dehydrogenases or amine oxidases in combination with one or more aldehyde generating enzymes such as an acyl-CoA reductase (e.g., Acr1) in the presence of a carbon source under conditions effective to express the fatty amines. In another embodiment, a fatty amine composition is produced by culturing host cells that express one or more of an exogenous biosynthetic enzyme (e.g., aminotransferases/transaminases or amine dehydrogenases or amine oxidases in combination with one or more aldehyde generating enzymes such as a phosphopanthetheinyl transferase (PPTase) in the presence of a carbon source under conditions effective to express the fatty amines.

Expression of the biosynthetic enzymes results in production of fatty amines with increased yields of fatty amines and/or fatty amine compositions or blends thereof. In one embodiment, expression of an aminotransferase or amine dehydrogenase polypeptide in the host cell results in a high yield of fatty amines or compositions thereof. In another embodiment, expression of an aminotransferase or amine dehydrogenase polypeptide in combination with one or more aldehyde generating enzymes in the host cell results in a high yield of fatty amines and compositions thereof. In another embodiment, expression of an amine oxidase in combination with one or more aldehyde generating enzymes in the host cell results in high yields of fatty amines and compositions thereof. In some embodiments, the biosynthetic enzymes are exogenously expressed in the cell.

The host cells or microorganisms of the disclosure may include host strains or host cells that are further genetically engineered to contain alterations in order to test the efficiency of specific mutations or manipulations on enzymatic activities (i.e., recombinant cells or microorganisms). Various optional genetic manipulations and alterations can be used interchangeably from one host cell to another, depending on what native enzymatic pathways are present in the original host cell. In one embodiment, a host strain can be used for testing the expression of an aminotransferase or amine dehydrogenase polypeptide in combination with an aldehyde generating polypeptide. A host strain may encompasses a number of genetic alterations in order to test specific variables, including but not limited to, culture conditions including fermentation components, carbon source (e.g., feedstock), temperature, pressure, reduced culture contamination conditions, and oxygen levels.

In one embodiment, a host strain encompasses an optional fadE and fhuA deletion. Acyl-CoA dehydrogenase (FadE) is an enzyme that is important for metabolizing fatty acids. It catalyzes the second step in fatty acid utilization (beta-oxidation), which is the process of breaking long chains of fatty acids (acyl-CoAs) into acetyl-CoA molecules. More specifically, the second step of the β-oxidation cycle of fatty acid degradation in bacteria is the oxidation of acyl-CoA to 2-enoyl-CoA, which is catalyzed by FadE. When $E.$ $coli$ lacks FadE, it cannot grow on fatty acids as a carbon source but it can grow on acetate. The inability to utilize fatty acids of any chain length is consistent with the reported phenotype of fadE strains, i.e., fadE mutant strains where FadE function is disrupted. The fadE gene can be optionally knocked out or attenuated to assure that acyl-CoAs, which may be intermediates in a fatty amine pathway, can accumulate in the cell such that all acyl-CoAs can be efficiently converted to fatty amines. However, fadE attenuation is optional when sugar is used as a carbon source since under such condition expression of FadE is likely repressed and FadE therefore may only be present in small amounts and not able to efficiently compete with ester synthase for acyl-CoA substrates. FadE is repressed due to catabolite repression. $E.$ $coli$ and other microbes prefer to consume sugar over fatty acids, so when both sources are available sugar is consumed first by repressing the fad regulon (see D. Clark, $J$ $Bacteriol.$ (1981) 148(2):521-6)). Moreover, the absence of sugars induces FadE expression. Acyl-CoA intermediates could be lost to the beta oxidation pathway since the proteins expressed by the fad regulon (including FadE) are up-regulated and will efficiently compete for acyl-CoAs. Thus, it can be beneficial under certain circumstances to have the fadE gene knocked out or attenuated. Since many carbon sources are carbohydrate based, it is optional to attenuate FadE. The gene fhuA codes for the TonA protein, which is an energy-coupled transporter and receptor in the outer membrane of $E.$ $coli$ (V. Braun (2009) $J$ $Bacteriol.$ 191(11): 3431-3436). Its deletion is optional. The fhuA deletion allows the cell to become more resistant to phage attack which can be beneficial in certain fermentation conditions. Thus, it may be desirable to delete fhuA in a host cell that is likely subject to potential contamination during fermentation runs.

In another embodiment, the host strain (supra) may also encompass optional overexpression of one or more of the following genes including fadR, fabA, fabD, fabG, fabH, fabV, and/or fabF. Examples of such genes are fadR from $Escherichia$ $coli$, fabA from $Salmonella$ $typhimurium$ (NP_460041), fabD from $Salmonella$ $typhimurium$ (NP_460164), fabG from $Salmonella$ $typhimurium$ (NP_460165), fabH from $Salmonella$ $typhimurium$ (NP_460163), fabV from $Vibrio$ $cholera$ (YP_001217283), and fabF from $Clostridium$ $acetobutylicum$ (NP_350156). The optional overexpression of one or more of these genes, which code for enzymes and regulators in fatty acid biosynthesis, can serve to increase the titer of fatty-acid derivative compounds under various culture conditions.

In another embodiment, $E.$ $coli$ strains are used as host cells for the production of fatty amines. Similarly, these host cells may provide optional overexpression of one or more biosynthesis genes (i.e., genes coding for enzymes and regulators of fatty acid biosynthesis) that can increase the titer of fatty-acid derivative compounds such as fatty amines under various culture conditions including, but not limited to, fadR, fabA, fabD, fabG, fabH, fabV and/or fabF. Examples of genetic alterations include fadR from $Escherichia$ $coli$, fabA from $Salmonella$ $typhimurium$ (NP_460041), fabD from $Salmonella$ $typhimurium$ (NP_460164), fabG from $Salmonella$ $typhimurium$ (NP_460165), fabH from $Salmonella$ $typhimurium$ (NP_460163), fabV from $Vibrio$ $cholera$ (YP_001217283), and fabF from $Clostridium$ $acetobutylicum$ (NP_350156).

In some embodiments, the host cells or microorganisms that are used to express the biosynthetic enzymes (e.g., aminotransferases or amine dehydrogenases in combination with aldehyde generating enzymes such as CAR and/or TE and/or AAR and/or PPTase) may further express genes that encompass certain enzymatic activities that can increase the production to one or more particular fatty acid derivative(s) such as fatty esters, fatty alcohols, fatty amines, fatty aldehydes, bifunctional fatty acid derivatives, diacids and the like. In one embodiment, the host cell has thioesterase activity (E.C. 3.1.2.* or E.C. 3.1. 2.14 or E.C. 3.1.1.5) for the production of fatty acids which can be increased by over-expressing the gene. In another embodiment, the host cell has ester synthase activity (E.C. 2.3.1.75) for the production of fatty esters. In another embodiment, the host cell has acyl-ACP reductase (AAR) (E.C. 1.2.1.80) activity and/or alcohol dehydrogenase activity (E.C. 1.1.1.1.) and/or fatty alcohol acyl-CoA reductase (FAR) (E.C. 1.1.1.*) activity and/or carboxylic acid reductase (CAR) (EC 1.2.99.6) activity for the production of fatty alcohols. In another embodiment, the host cell has acyl-ACP reductase (AAR) (E.C. 1.2.1.80) activity for the production of fatty aldehydes. In another embodiment, the host cell has acyl-ACP reductase (AAR) (E.C. 1.2.1.80) activity and decarbonylase activity for the production of alkanes and alkenes. In another embodiment, the host cell has acyl-CoA reductase (E.C. 1.2.1.50) activity, acyl-CoA synthase (FadD) (E.C. 2.3.1.86) activity, and thioesterase (E.C. 3.1.2.* or E.C. 3.1. 2.14 or E.C. 3.1.1.5) activity for the production of fatty alcohols. In another embodiment, the host cell has ester synthase activity (E.C. 2.3.1.75), acyl-CoA synthase (FadD) (E.C. 2.3.1.86) activity, and thioesterase (E.C. 3.1.2.* or E.C. 3.1. 2.14 or E.C. 3.1.1.5) activity for the production of fatty esters. In another embodiment, the host cell has OleA activity for the production of ketones. In another embodiment, the host cell has OleBCD activity for the production of internal olefins. In another embodiment, the host cell has acyl-ACP reductase (AAR) (E.C. 1.2.1.80) activity and alcohol dehydrogenase activity (E.C. 1.1.1.1.) for the production of fatty alcohols. In another embodiment, the host cell has thioesterase (E.C. 3.1.2.* or E.C. 3.1. 2.14 or E.C. 3.1.1.5) activity and decarboxylase activity for making terminal olefins. The expression of enzymatic activities in microorganisms and microbial cells is taught by U.S. Pat. Nos. 8,097,439; 8,110,093; 8,110,670; 8,183,028; 8,268,599; 8,283,143; 8,232,924; 8,372,610; and 8,530,221, which are incorporated herein by reference.

In other embodiments, the host cells or microorganisms that are used to express the biosynthetic enzymes (e.g., aminotransferases or amine dehydrogenases in combination with aldehyde generating enzymes such as CAR and/or TE and/or AAR and/or PPTase) will include certain native enzyme activities that are upregulated or overexpressed in order to produce one or more particular fatty acid derivative(s) such as fatty amines. In one embodiment, the host cell has a native thioesterase (E.C. 3.1.2.* or E.C. 3.1. 2.14 or E.C. 3.1.1.5) activity for the production of fatty acids which can be increased by overexpressing the thioesterase gene.

The present disclosure includes host strains or microorganisms that express genes that code for the biosynthetic enzymes (e.g., aminotransferases or amine dehydrogenases in combination with aldehyde generating enzymes such as CAR and/or TES and/or AAR and/or PPTase). In one embodiment, at least one biosynthetic enzyme is exogenously expressed in the host cell. For example, the host cell may express an exogenous aminotransferase in order to produce fatty amines. In another embodiment, one or more biosynthetic enzymes are exogenously expressed in the host cell. For example, the host cell may express an exogenous aminotransferase and an exogenous carboxylic acid reductase (CAR) in order to produce fatty amines. In still another embodiment, one or more biosynthetic enzymes are exogenously expressed in the host cell in combination with one or more biosynthetic enzymes that are overexpressed in the host cell. For example, the host cell may express an exogenous aminotransferase and an exogenous carboxylic acid reductase (CAR) in combination with an exogenous and/or overexpressed thioesterase in order to produce fatty amines. The thioesterase may be an exogenously expressed thioesterase. Alternatively, the thioesterase may be a native thioesterase that is overexpressed or transcriptionally upregulated in the cell via a particularly strong promoter or other molecular biology techniques that are well known to those of skill in the art. The recombinant host cells produce fatty amines and compositions and blends thereof. The fatty amines are typically recovered from the culture medium and/or are isolated from the host cells. In one embodiment, the fatty amines are recovered from the culture medium (extracellular). In another embodiment, the fatty amines are isolated from the host cells (intracellular). In another embodiment, the fatty amines are recovered from the culture medium and isolated from the host cells. The fatty amine composition produced by a host cell can be analyzed using methods known in the art, for example, GC-FID, in order to determine the distribution of particular fatty amines as well as chain lengths and degree of saturation of the components of the fatty amine composition.

Examples of host cells that function as microorganisms (e.g., microbial cells), include but are not limited to cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* or *Streptomyces*. In some embodiments, the host cell is a Gram-positive bacterial cell. In other embodiments, the host cell is a Gram-negative bacterial cell. In some embodiments, the host cell is an *E. coli* cell. In some embodiment, the host cell is an *E. coli* B cell, an *E. coli* C cell, an *E. coli* K cell, or an *E. coli* W cell. In other embodiments, the host cell is a *Bacillus lentus* cell, a *Bacillus brevis* cell, a *Bacillus stearothermophilus* cell, a *Bacillus lichenoformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In still other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell. In yet other embodiments, the host cell is a *Streptomyces lividans* cell or a *Streptomyces murinus* cell. In yet other embodiments, the host cell is an *Actinomycetes* cell. In some embodiments, the host cell is a *Saccharomyces cerevisiae* cell.

In other embodiments, the host cell is a cell from a eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell has autotrophic activity.

In some embodiments, the host cell has photoautotrophic activity, such as in the presence of light. In some embodiments, the host cell is heterotrophic or mixotrophic in the absence of light. In certain embodiments, the host cell is a cell from *Arabidopsis thaliana, Panicum virgatum, Miscanthus giganteus, Zea mays, Botryococcuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus elongates* BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridium thermocellum, Penicillium chrysogenum, Pichia pastoris, Saccharomyces cerevisiae, Schizosaccharomyces pombe, Pseudomonas fluorescens,* or *Zymomonas mobilis*.

In one particular embodiment, the microbial cell is from a cyanobacteria including, but not limited to, *Prochlorococcus, Synechococcus, Synechocystis, Cyanothece,* and *Nostoc punctiforme*. In another embodiment, the microbial cell is from a specific cyanobacterial species including, but not limited to, *Synechococcus elongatus* PCC7942, *Synechocystis* sp. PCC6803, and *Synechococcus* sp. PCC7001.

Methods of Making Recombinant Host Cells and Cultures

Various methods well known in the art can be used to engineer host cells to produce fatty amines and/or fatty amine compositions or blends. The methods can include the use of vectors, preferably expression vectors, including a nucleic acid encoding the biosynthetic enzyme (e.g., aminotransferases or amine dehydrogenases alone or in combination with aldehyde generating enzymes such as CAR and/or TE and/or AAR and/or PPTase), as described herein. Those skilled in the art will appreciate a variety of viral and non-viral vectors can be used in the methods described herein.

In some embodiments of the present disclosure, a higher titer of fatty amines in a particular composition is a higher titer of a particular type of fatty amine or a combination of fatty amines produced by a recombinant host cell culture relative to the titer of the same fatty acid amine or combination of fatty amine produced by a control culture of a corresponding wild-type host cell. In some embodiments, biosynthetic polypeptides (e.g., aminotransferases or amine dehydrogenases alone or in combination with polypeptides of aldehyde generating enzymes such as CAR and/or TE and/or AAR and/or PPTase) are provided to the host cell by way of a recombinant vector, which may include a promoter operably linked to a specific polynucleotide sequence that codes for a specific biosynthetic polypeptide. In certain embodiments, the promoter is a developmentally-regulated, an organelle-specific, a tissue-specific, an inducible, a constitutive, or a cell-specific promoter. The recombinant vector typically comprises at least one sequence selected from an expression control sequence operatively coupled to the polynucleotide sequence; a selection marker operatively coupled to the polynucleotide sequence; a marker sequence operatively coupled to the polynucleotide sequence; a purification moiety operatively coupled to the polynucleotide sequence; a secretion sequence operatively coupled to the polynucleotide sequence; and a targeting sequence operatively coupled to the polynucleotide sequence. The polynucleotide sequences, comprising open reading frames encoding proteins and operably-linked regulatory sequences can be integrated into a chromosome of the recombinant host cells, incorporated in one or more plasmid expression system resident in the recombinant host cells, or both.

The expression vectors include a polynucleotide sequence as described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein. Expression of genes encoding polypeptides in prokaryotes, for example, E. coli, is most often carried out with vectors containing constitutive or inducible promoters directing the expression of either fusion or non-fusion polypeptides. Suitable expression systems for both prokaryotic and eukaryotic cells are well known in the art (see, e.g., Sambrook et al., "Molecular Cloning: A Laboratory Manual," second edition, Cold Spring Harbor Laboratory, (1989)). In certain embodiments, a polynucleotide sequence of the disclosure is operably linked to a promoter derived from bacteriophage T5. In one embodiment, the host cell is a yeast cell. In this embodiment, the expression vector is a yeast expression vector. Vectors can be introduced into prokaryotic or eukaryotic cells via a variety of art-recognized techniques for introducing foreign nucleic acid (e.g., DNA) into a host cell. Suitable methods for transforming or transfecting host cells can be found in, for example, Sambrook et al. (supra).

For stable transformation of bacterial cells, it is known that, depending upon the expression vector and transformation technique used, only a small fraction of cells will take-up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transformed with the introduced nucleic acid can be identified by growth in the presence of an appropriate selection drug.

Culture and Fermentation of Recombinant Host Cells

As used herein, the term "fermentation" broadly refers to the conversion of organic materials into target substances by host cells, for example, the conversion of a carbon source by recombinant host cells into fatty amines or derivatives thereof by propagating a culture of the recombinant host cells in a media comprising the carbon source. As used herein, the term "conditions permissive for the production" means any conditions that allow a host cell to produce a desired product, such as a fatty amine or fatty amine composition or blend. Similarly, the term "conditions in which the polynucleotide sequence of a vector is expressed" means any conditions that allow a host cell to synthesize a polypeptide. Suitable conditions include, for example, fermentation conditions. Fermentation conditions can comprise many parameters, including but not limited to temperature ranges, levels of aeration, feed rates and media composition. Each of these conditions, individually and in combination, allows the host cell to grow. Fermentation can be aerobic, anaerobic, or variations thereof (such as micro-aerobic). Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source.

For small scale production, the engineered host cells can be grown in batches of, for example, about 100 µL, 200 µL, 300 µL, 400 µL, 500 µL, 1 mL, 5 mL, 10 mL, 15 mL, 25 mL, 50 mL, 75 mL, 100 mL, 500 mL, 1 L, 2 L, 5 L, or 10 L; fermented; and induced to express a desired polynucleotide sequence, such as a polynucleotide sequence encoding an aminotransferase/transaminase or an amine dehydrogenase or an amine oxidase polypeptide alone or in combination with an aldehyde-generating polynucleotide sequence encoding a CAR and/or a TE and/or an AAR and/or a PPtase polypeptide. For large scale production, the engineered host cells can be grown in cultures having volume batches of about 10 L, 100 L, 1000 L, 10,000 L, 100,000 L, 1,000,000 L or larger; fermented; and induced to express a desired polynucleotide sequence. In one preferred embodiment, the fatty amines and fatty amine derivative compositions described herein are found in the extracellular environment of the recombinant host cell culture and can be readily isolated from the culture medium. In another embodiment, the fatty amines and fatty amine derivative compositions described herein are found in the intracellular environment of the recombinant host cells grown in culture. A fatty amine or derivative thereof may be secreted by the recombinant host cell, transported into the extracellular environment or passively transferred into the extracellular environment of the recombinant host cell culture. The fatty amine composition may be isolated from a recombinant host cell culture using routine methods known in the art.

Screening Recombinant Host Cells

In one embodiment of the present disclosure, the activity of an aminotransferase/transaminase or an amine dehydrogenase or an amine oxidase polypeptide is determined by culturing recombinant host cells encompassing one or more aminotransferase/transaminase or amine dehydrogenase or amine oxidase polypeptide sequences (optionally in combination with one or more aldehyde-generating polypeptides), followed by screening to identify characteristics of, for example, fatty amine compositions produced by the recombinant host cells; for example, titer, yield and productivity of fatty amines and compositions and blends thereof. In another embodiment, the activity of a aminotransferase/transaminase or amine dehydrogenase or amine oxidase polypeptide is determined by culturing recombinant host cells encompassing one or more aminotransferase/transaminase or amine dehydrogenase or amine oxidase polynucleotide sequences, followed by screening to identify characteristics of, for example, fatty amine compositions produced by the recombinant host cells; for example: titer, yield and productivity of fatty amines and compositions and blends thereof. The aminotransferase/transaminase or amine dehydrogenase or amine oxidase polypeptides and fragments thereof can be assayed for their activity in a cell and/or improved/increased production of amine-derived compounds using routine methods known in the art. For example, an aminotransferase/transaminase or an amine dehydrogenase or an amine oxidase polypeptide or fragment thereof is contacted with a substrate in vivo (e.g., a fatty aldehyde produced by coexpressing CAR and/or TE and/or AAR and/or PPTase in the cell) under conditions that allow the polypeptide to function and carry out its enzymatic activity. A decrease in the level of the substrate or an increase in the level of a fatty amine or a fatty amine composition can be measured to determine the activity of the aminotransferase/transaminase or amine dehydrogenase or amine oxidase. Alternatively, a cell expressing an aminotransferase/transaminase or an amine dehydrogenase or an amine oxidase polypeptide or fragment thereof can be fed with a fatty aldehyde substrate under conditions that still allow the polypeptide to function and carry out its enzymatic activity. An increase in the level of a fatty amine or a fatty amine composition can then be measured to determine the activity of the aminotransferase/transaminase or amine dehydrogenase or amine oxidase.

Products Derived from Recombinant Host Cells

As used herein, "fraction of modern carbon" or fM has the same meaning as defined by National Institute of Standards and Technology (NIST) Standard Reference Materials (SRMs 4990B and 4990C, known as oxalic acids standards HOxI and HOxII, respectively. The fundamental definition relates to 0.95 times the 14C/12C isotope ratio HOxI (referenced to AD 1950). This is roughly equivalent to decay-corrected pre-Industrial Revolution wood. For the current living biosphere (plant material), fM is approximately 1.1.

Bioproducts (e.g., the fatty amine compositions produced in accordance with the present disclosure) comprising biologically produced organic compounds, and in particular, the fatty amine compositions produced using the biosynthetic pathway herein, have been produced from renewable sources and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol, etc.) can be determined by dual carbon-isotopic fingerprinting (see, e.g., U.S. Pat. No. 7,169,588). The ability to distinguish bioproducts from petroleum based organic compounds is beneficial in tracking these materials in commerce. For example, organic compounds or chemicals comprising both biologically based and petroleum based carbon isotope profiles may be distinguished from organic compounds and chemicals made only of petroleum based materials. Hence, the bioproducts produced herein can be followed or tracked in commerce on the basis of their unique carbon isotope profile. Bioproducts can be distinguished from petroleum based organic compounds by comparing the stable carbon isotope ratio ($^{13}C/^{12}C$) in each sample. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, C3 plants (the broadleaf), C4 plants (the grasses), and marine carbonates all show significant differences in $^{13}C/^{12}C$ and the corresponding $\delta^{13}C$ values. Both C4 and C3 plants exhibit a range of $^{13}C/^{12}C$ isotopic ratios, but typical values are about −7 to about −13 per mil for C4 plants and about −19 to about −27 per mil for C3 plants (see, e.g., Stuiver et al. (1977) *Radiocarbon* 19:355). Coal and petroleum fall generally in this latter range.

$$\delta^{13}C(\%_o)=[(^{13}C/^{12}C)\text{sample}-(^{13}C/^{12}C)\text{standard}]/(^{13}C/^{12}C)\text{standard}\times 1000$$

A series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46. The compositions described herein include fatty amine compositions and products produced by any of the methods described herein. Specifically, fatty amine composition or product can have a $\delta^{13}C$ of about −28 or greater, about −27 or greater, −20 or greater, −18 or greater, −15 or greater, −13 or greater, −10 or greater, or −8 or greater. For example, the fatty amine composition or product can have a $\delta^{13}C$ of about −30 to about −15, about −27 to about −19, about −25 to about −21, about −15 to about −5, about −13 to about −7, or about −13 to about −10. In other instances, the fatty amine composition or product can have a $\delta^{13}C$ of about −10, −11, −12, or −12.3. Fatty amine compositions and products produced in accordance with the disclosure herein can also be distinguished from petroleum based organic compounds by comparing the amount of $^{14}C$ in each compound. Because $^{14}C$ has a nuclear half-life of 5730 years, petroleum based fuels containing "older" carbon can be distinguished from fatty amine compositions and bioproducts which contain "newer" carbon (see, e.g., Currie, "Source Apportionment of Atmospheric Particles", Characterization of Environmental Particles, J. Buffle and H. P. van Leeuwen, Eds., 1 of Vol. I of the IUPAC Environmental Analytical Chemistry Series (Lewis Publishers, Inc.) 3-74, (1992)).

The basic assumption in radiocarbon dating is that the constancy of $^{14}C$ concentration in the atmosphere leads to the constancy of $^{14}C$ in living organisms. However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about 1.2×10-12, with an approximate relaxation "half-life" of 7-10 years. This latter half-life must not be taken literally;

rather, one must use the detailed atmospheric nuclear input/decay function to trace the variation of atmospheric and biospheric $^{14}C$ since the onset of the nuclear age. It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" (fM). The fatty amine compositions and products described herein include bioproducts that can have an fM $^{14}C$ of at least about 1. For example, the bioproduct of the disclosure can have an fM $^{14}C$ of at least about 1.01, an fM $^{14}C$ of about 1 to about 1.5, an fM $^{14}C$ of about 1.04 to about 1.18, or an fM $^{14}C$ of about 1.111 to about 1.124.

Another measurement of $^{14}C$ is known as the percent of modern carbon (pMC). For an archaeologist or geologist using $^{14}C$ dates, AD 1950 equals "zero years old". This also represents 100 pMC. "Bomb carbon" in the atmosphere reached almost twice the normal level in 1963 at the peak of thermo-nuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC. A biologically based carbon content is derived by assigning "100%" equal to 107.5 pMC and "0%" equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material. A bioproduct comprising one or more fatty amines as described herein can have a pMC of at least about 50, 60, 70, 75, 80, 85, 90, 95, 96, 97, 98, 99, or 100. In other instances, a fatty ester composition described herein can have a pMC of between about 50 and about 100; about 60 and about 100; about 70 and about 100; about 80 and about 100; about 85 and about 100; about 87 and about 98; or about 90 and about 95. In yet other instances, a fatty amine composition described herein can have a pMC of about 90, 91, 92, 93, 94, or 94.2.

Fatty Amine Compositions

The structure of fatty amines is based on one or more C8 to C24 aliphatic alkyl groups ($R=C_8-C_{24}$) and one or more amine (N) or quaternary ammonium. The aliphatic alkyl chain is strongly hydrophobic while the amine is hydrophilic. Thus, the fatty amine has an amphiphilic nature as a molecule (containing both hydrophobic and hydrophilic entities). When dissolved in water or other solvents, fatty amines form micelles because one part of the molecule is repelled by the solvent. As such, fatty amines are cationic surface-active compounds (i.e., surfactants that are characterized by their hydrophilic moiety) which strongly adhere to surfaces by either physical or chemical bonding, thus modifying surface properties. The surface active properties of fatty amines are emulsification, wetting, foaming, and thickening. In addition, fatty amines have adsorptive properties including softening, adhesion, lubrication, corrosion inhibition, anti-static properties and hydrophobation; as well as reactive properties including ion exchange, decolorization, and flocculation.

The present disclosure contemplates the production of fatty amines and derivatives thereof that are useful in many industrial applications including as chemical intermediates, as processing aids, and as functional components in numerous formulations. Examples of fatty amines include those produced in the present host cells and derived from fatty aldehyde precursors as described herein. The fatty amines and/or fatty amine compositions or blends that are produced herein can be used, individually or in suitable combinations or blends. The fatty amines of the present disclosure find use in industrial applications including, but not limited to, detergents (cleaners, thickeners, fabric softeners); dishwashing liquids; foaming- and wetting agents; demulsifiers (pharmaceuticals, paper, petroleum); emulsifiers (solvents, solvent cleaners, silicones, oil, wax polish, leather treatment, triglycerides); surfactants; shampoos and conditioners; anti-static agents in the textile and plastics industry (textiles, polymers, electronics, electrostatic sprays, paper); fuel additives; lubricants and lubricant additives (grease thickeners, engine oil); paint thickeners; mineral processing; paper manufacture; petroleum production and refining (petroleum additives, oil field chemicals); asphalt emulsifiers; corrosion inhibitors (acid, water treatment, metal workings, petroleum); gasoline- and fuel oil additives; flotation agents; epoxy curing agents; and agricultural chemicals and herbicides. In some aspects, the disclosure pertains to a method of producing a fatty amine composition including fatty amines that are made of either a mixture of carbon chains or a specific chain length that ranges from about C8 to about C24. In one particular aspect, the disclosure pertains to a method of producing a fatty amine composition encompassing primary fatty amines ($RNH_2$). In another aspect, secondary fatty amines ($R_2NH$) and/or tertiary fatty amines (trialkyl ($R_3N$), dialkylmethyl ($R_2NCH_3$), and/or alkyldimethyl ($RN(CH_3)_2$)) are also contemplated. In another aspect, the present disclosure encompasses the production of primary amines that can become the primary building blocks for many industrial products as well as provide the source material for numerous chemical derivatives such as polyamines, ethoxylated amines, ethoxylated diamines, propoxylated amines, amine salts, amine oxides, amides, ethoxylated amides, and nitriles. In related aspects, the method encompasses a genetically engineered production host suitable for making fatty amines and fatty amine compositions including, but not limited to, primary amines that are suitable for producing chemical derivatives and compositions thereof including, but not limited to, polyamines, ethoxylated amines, ethoxylated diamines, propoxylated amines, amine salts, amine oxides, amides, ethoxylated amides, and nitriles.

In general, the fatty amine or fatty amine composition of the present disclosure is isolated from the extracellular environment of the host cell. In some embodiments, the fatty amine or fatty amine composition is spontaneously secreted, partially or completely, from the host cell. In alternative embodiments, the fatty amine or fatty amine composition is transported into the extracellular environment, optionally with the aid of one or more transport proteins. In still other embodiments, the fatty amine or fatty amine composition is passively transported into the extracellular environment.

The methods can produce fatty amines including a C8-C24 fatty amine. In some embodiments, the fatty amine includes a C8, C9, C10, C11, C12, C13, C14, C15, C16, C17, C18, C19, C20, C21, C22, C23 and/or C24 fatty amine. In other embodiments, the fatty amine composition includes one or more of a C6, C7, C8, C9, C10, C11, C12, C13, C14, C15, C16, C17, and a C18 fatty amine. In still other embodiments, the fatty amine composition includes C12, C14, C16 and C18 fatty amines; C12, C14 and C16 fatty amines; C14, C16 and C18 fatty amines; or C12 and C14 fatty amines. The R group of a fatty amine, can be a straight chain or a branched chain. Branched chains may have more than one point of branching and may include cyclic branches. In some embodiments, the branched fatty amine is a C6, C7, C8, C9, C10, C11, C12, C13, C14, C15, C16, C17, C18, C19, C20, C21, C22, C23 or C24 branched fatty amine. The R group of a branched or unbranched fatty amine can be saturated or unsaturated. If unsaturated, the R group can have one or more than one point of unsaturation. In some embodiments, the unsaturated fatty amine is a monounsaturated fatty amine. In certain embodiments, the unsaturated fatty amine is a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1 or a C24:1 unsaturated fatty amine. In certain embodiments, the unsaturated fatty amine is a C10:1, C12:1, C14:1, C16:1, or C18:1 unsaturated fatty amine. In other embodiments, the unsaturated fatty amine is unsaturated at the omega-7 position. In certain embodiments, the unsaturated fatty amine has a cis double bond.

In one preferred embodiment, the fatty amine is a primary amine including, but not limited to, octyl amine, decyl amine, dodecyl amine, tetradecyl amine, hexadecyl amine, octadecyl amine, stearyl amine, and oleyl amine. In another embodiment, the fatty amine is a secondary amine, for example, 1-dodecylamine (laurylamine), 1-hexadecylamine (palmitylamine), 1-octadecylamine (stearylamine), and the like. In another embodiment, the fatty amine is a tertiary amine, for example, 1-octadecen-9-ylamine (oleylamine), and the like. Other examples of fatty amines are alkyl dimethyl amines including, but not limited to, octyl dimethyl amine, decyl dimethyl amine, dodecyl dimethyl amine, tetradecyl dimethyl amine, hexadecyl dimethyl amine, octadecyl dimethyl amine, and oleyl dimethyl amine. Still other examples of fatty amines are dialkyl methyl amines including, but not limited to, dioctyl methyl amine, didecyl methyl amine, didodecyl methyl amine, ditetradecyl methyl amine, dihexadecyl methyl amine, and dioctadecyl methyl amine. The disclosure further contemplates fatty amines produced by the recombinant host cells as described herein that can be used for chemical derivatives, such as fatty amides (e.g., stearamide, oleamide, erucamide); quaternaries (e.g., tetramethyl ammonium chloride, tetramethyl ammonium bromide, tetraethyl ammonium bromide, tetrapropyl ammonium bromide); and ethoxylates (e.g., lauryl amine, stearyl amine, oleyl amine, octadecyl amine).

In other embodiments, the fatty amine includes a straight-chain fatty amine. In other embodiments, the fatty amine includes a branched-chain fatty amine. In yet other embodiments, the fatty amine comprises a cyclic moiety. In some embodiments, the fatty amine is an unsaturated fatty amine. In other embodiments, the fatty amine is a monounsaturated fatty amine. In yet other embodiments, the fatty amine is a saturated fatty amine. In another aspect, the disclosure features a fatty amines produced by any of the methods or any of the microorganisms described herein, or a surfactant encompassing a fatty amine produced by any of the methods or any of the microorganisms described herein. In some embodiments, the fatty amine has a $\delta^{13}C$ of about −15.4 or greater. In certain embodiments, the fatty amine has a $\delta^{13}C$ of about −15.4 to about −10.9, or of about −13.92 to about −13.84. In some embodiments, the fatty amines has an $f_M{}^{14}C$ of at least about 1.003. In certain embodiments, the fatty amine has an $f_M{}^{14}C$ of at least about 1.01 or at least about 1.5. In some embodiments, the fatty amine has an $f_M{}^{14}C$ of about 1.111 to about 1.124.

EXAMPLES

The following specific examples are intended to illustrate the disclosure and should not be construed as limiting the scope of the claims.

Example 1

Fatty aldehyde precursors and corresponding fatty amines were generated in vivo by co-expressing a thioesterase ('tesA) and a carboxylic acid reductase (CarB) with a putrescine aminotransferase (ygjG) along with supplementation of a nitrogen source (glutamate). The fatty aldehyde precursors were converted into the corresponding amines.

The ygjG gene was cloned from the *E. coli* MG1655 strain via PCR with the following primers:

```
Forward primer:
                                (SEQ ID NO: 1)
'5-AGGAGGAATAACATATGAACAGGTTACCTTCGAGCGCATCGGC-3'.

Reverse primer:
                                (SEQ ID NO: 2)
'5-CCCAAGCTTCGAATTCTTACGCTTCTTCGACACTTACTCGCATGGC
C-3'.
```

The ygjG gene was then ligated into the expression vector pACYC (i.e., high copy expression vector), to generate the plasmid pACYC-ygjG. A second plasmid was generated and named pCL1920-CarB-18-cTesA2-13C05 (i.e., low copy plasmid), which contained the *Mycobacterium smegmatis* carB gene and a variant of the thioesterase gene ('tesA) from *E. coli*. The two plasmids were co-transformed into an *E. coli* strain that does not produce fatty amines (DVD2.1, containing ΔfadE ΔtonA fabB-A329V $P_{T5}$-entD from the *E. coli* MG1655 strain) giving strain F16-YG. The host cells were also transformed with each of the plasmids separately for use as controls giving control strains F16 (pCL1920-CarB-18-cTesA2-13C05) and control strain YG (pACYC-ygjG).

The cells were grown at 32° C. in M9 minimal medium supplemented with 3% (w/v) glucose, 0.5% (v/v) TRITON X-100, 0.1 M bis-tris, pH 7.0, and induced at $OD_{600}$~1.0 with 1 mM isopropyl β-D-1-thiogalactopyranoside (IPTG). (IPTG triggers transcription of the lac operon, and is used to induce protein expression where the gene is under the control of the lac operator.) At the time of induction, 5 g/L L-glutamate was also added as a source of nitrogen. Strains containing pACYC-ygjG were grown in the presence of the antibiotic carbenicillin, and strains containing pCL1920-CarB-18-cTesA2-13C05 were grown in the presence of spectinomycin, in order to select for the respective plasmids. After overnight growth, the cultures of the three strains were supplemented with an additional 10 g/L glucose and 5 g/L L-glutamate. Aliquots of 1 mL of culture were frozen at 24 hours post-induction.

Figure 2:
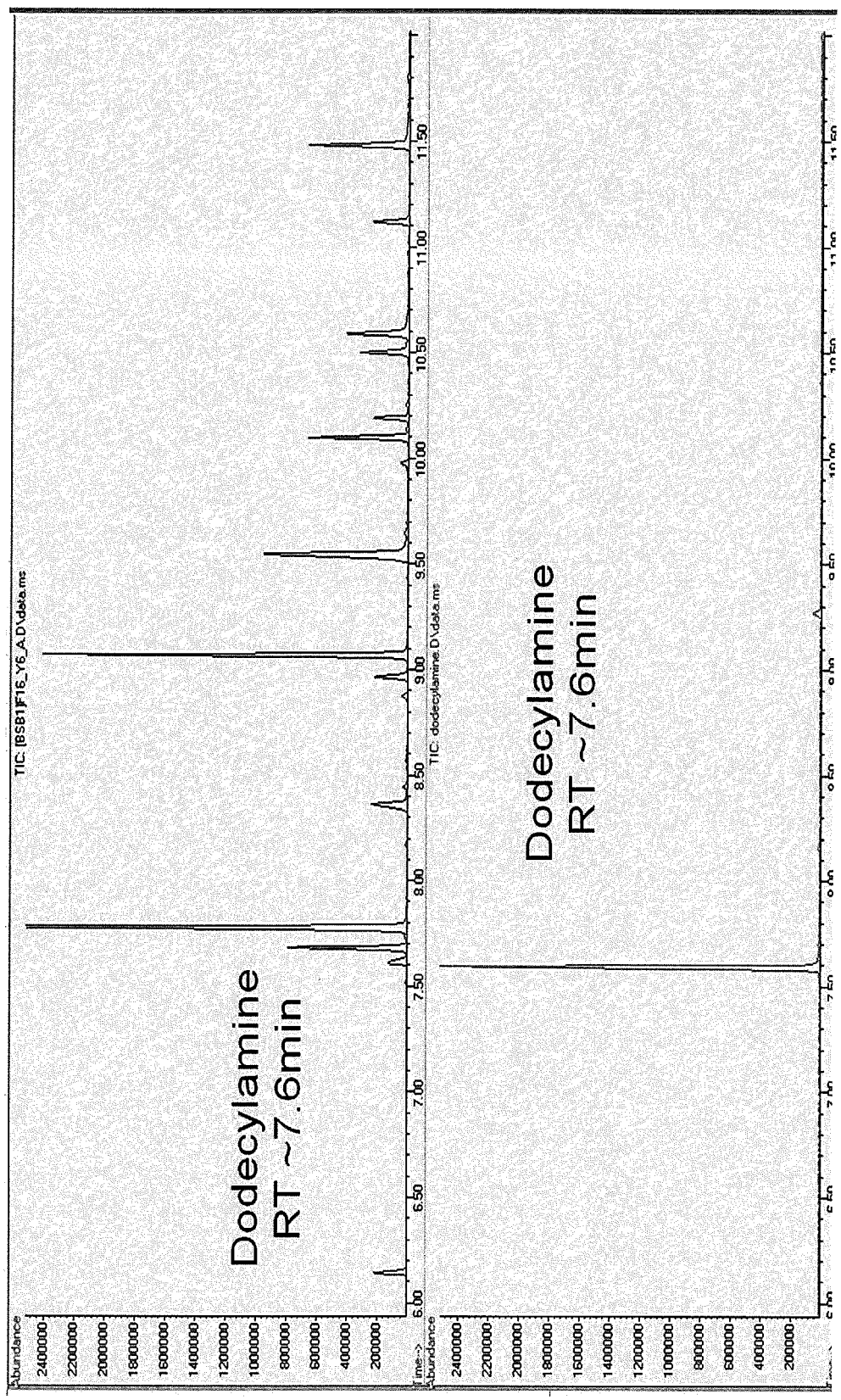
FIG. 2 depicts another MS/GC chromatograph showing the elution profile of the F16-YG sample (top row) as compared to the 1-dodecylamine reference standard (bottom row). Additional peaks in the top and middle rows are fatty alcohols.
Figure 3:
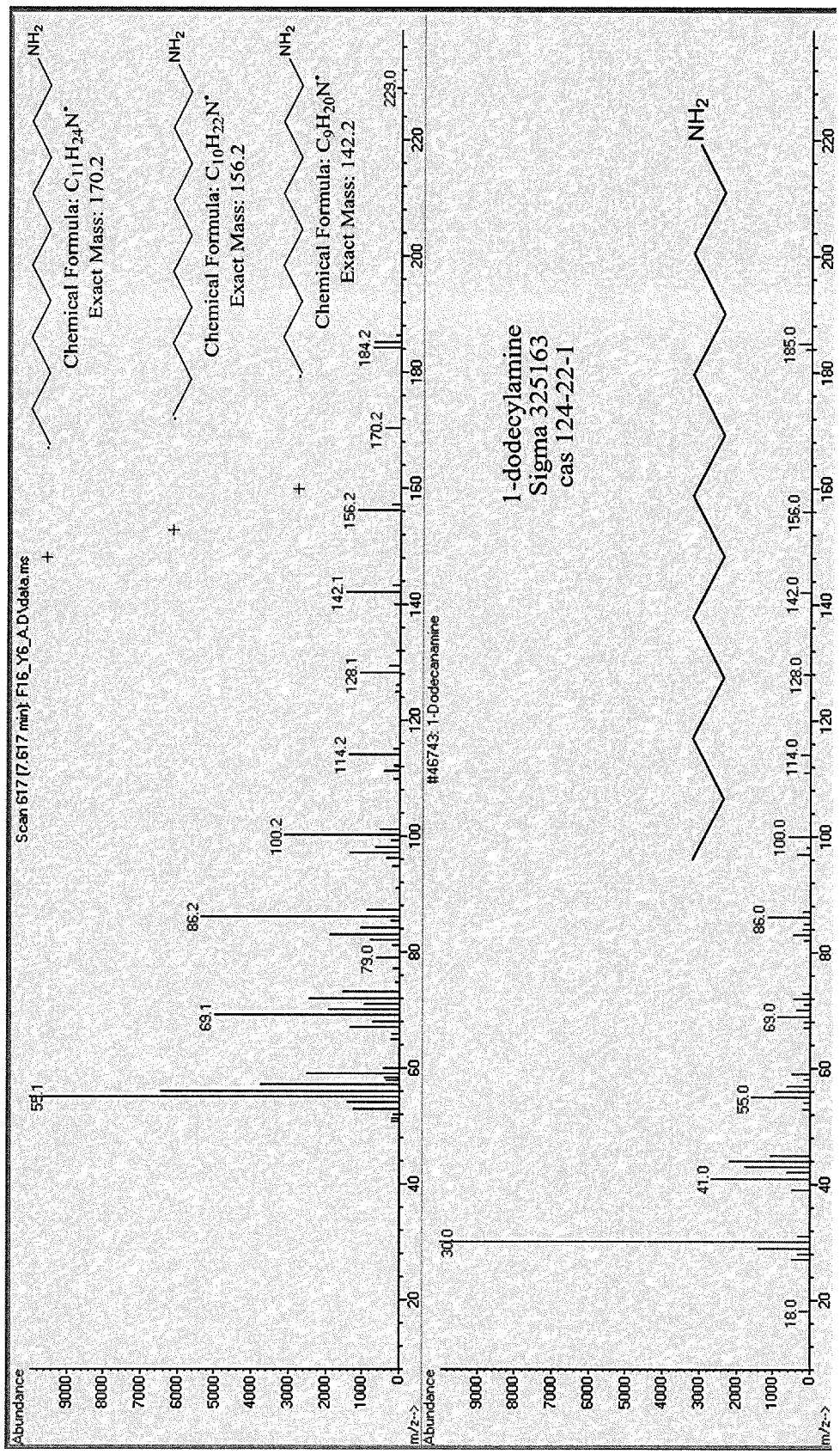
FIG. 3 shows the ion fragmentation pattern of the 7.6 minutes peak from the F16-YG sample (top row) and the 1-dodecylamine reference standard (bottom row). The molecular structure of characteristic ion fragments of 1-dodecylamine, including $C_{11}H_{24}N$, $C_{10}H_{22}N$, $C_9H_{20}N$, are also shown in the top row.

In order to prepare samples for analysis, 0.5 mL of ethyl acetate were added to each aliquot of culture. The samples were then vortexed at maximum speed for 15 minutes and centrifuged for 5 minutes. The organic phase was analyzed with a Gas Chromatograph Mass Spectrometry (GCMS from Agilent 6890) in EI mode (i.e., method: alkane 1 splitless CTC). The F16-YG strain, in which ygjG, carB, and 'tesA were exogenously expressed, yielded a unique peak at 7.6 minutes (FIG. 1 middle panel) that was not observed in either of the YG or F16 negative controls (FIG. 1 top and bottom panel). The unique peak in the sample from the F16-YG culture at 7.6 minutes was identified as 1-dodecylamine by the NIST 05 chemical compound library. An analytical reference standard purchased from Sigma/Aldrich (Product #325163) was run back to back with the F16-YG sample, which confirmed the identity of the compound as 1-dodecylamine by its retention time (FIG. 2) and by its ion fragmentation pattern (FIG. 3) showing characteristic fragments at m/z=142, 156 and 170 and a molecular ion at 185.

Example 2

Fatty aldehyde precursors and corresponding fatty amines can be generated in vivo by co-expressing an acyl-ACP reductase (AAR) with a putrescine aminotransferase (ygjG) along with supplementation of a nitrogen source (glutamate). The fatty aldehyde precursors can be converted into the corresponding amines.

The ygjG gene can be cloned from the *E. coli* MG1655 strain via PCR with the following primers:

```
Forward primer:
                                     (SEQ ID NO: 1)
'5-AGGAGGAATAACATATGAACAGGTTACCTTCGAGCGCATCGGC-3'.

Reverse primer:
                                     (SEQ ID NO: 2)
'5-CCCAAGCTTCGAATTCTTACGCTTCTTCGACACTTACTCGCATGGC
C-3'.
```

The ygjG gene can then then be ligated into the expression vector pACYC, to generate the plasmid pACYC-ygjG. A second plasmid can be generated and named pCL1920-aar, which is a pCL-based plasmid containing a gene for AAR from *Synechococcus elongatus* PCC7942 (aar). The two plasmids can be co-transformed into the *E. coli* strain that does not produce fatty amines (supra) giving strain F17-YG. The host cells can also be transformed with each of the plasmids separately for use as controls giving control strain F17 (pCL1920-aar) and control strain YG (pACYC-ygjG).

The cells can be grown at 32° C. in M9 minimal medium supplemented with 3% (w/v) glucose, 0.5% (v/v) TRITON X-100, 0.1 M bis-tris, pH 7.0, and induced at $OD_{600}$~1.0 with 1 mM isopropyl β-D-1-thiogalactopyranoside (IPTG). At the time of induction, 5 g/L L-glutamate can be also added as a source of nitrogen. Strains containing pACYC-ygjG can be grown in the presence of the antibiotic carbenicillin (0.05 mg/mL), and strains containing pCL1920-aar can be grown in the presence of 0.1 mg/mL spectinomycin in order to select for the respective plasmids. After overnight growth, the cultures of the three strains can be supplemented with an additional 10 g/L glucose and 5 g/L L-glutamate. Aliquots of 1 mL of culture can be frozen at 24 hours post-induction.

In order to prepare samples for analysis, 0.5 mL of ethyl acetate can be added to each aliquot of culture. The samples can then be vortexed at maximum speed for about 15 minutes and centrifuged for about 5 minutes as needed. The organic phase can be analyzed with a Gas Chromatograph Mass Spectrometry (GCMS from Agilent 6890) in EI mode (i.e., method: alkane 1 splitless CTC). The F17-YG strain, in which ygjG and/or aar are exogenously expressed, are expected to yield one or more unique peaks that represent fatty amines similar to what was observed in Example 1 (supra) and that were not observed in either of the YG or F17 negative controls. Any unique peaks in the sample from the F17-YG culture can be identified as fatty amines via the NIST 05 chemical compound library. For comparison, an analytical reference standard from Sigma/Aldrich (Product #325163) can be run back to back with the F17-YG sample, in order to confirm the identity of the compound being produced by its retention time and by its ion fragmentation pattern.

Example 3

Fatty aldehyde precursors and corresponding fatty amines can be generated in vivo by co-expressing a thioesterase (TesA) and a carboxylic acid reductase (CarB) with a GABA aminotransferase (PuuE) along with supplementation of a nitrogen source (glutamate). The fatty aldehyde precursors can be converted into the corresponding amines. The puuE gene can be cloned from an *E. coli* strain via PCR with a suitable forward and reverse primer (similarly as taught in Examples 1 and 2, supra). The puuE gene can then be ligated into an expression vector (e.g., pACYC, supra), to generate the plasmid pACYC-puuE. A second plasmid can be generated and named pCL1920-CarB-18-cTesA2-13C05, which is a second expression vector containing the *Mycobacterium smegmatis* carB gene and a variant of the thioesterase gene ('tesA) from *E. coli* (see Example 1, supra). The two plasmids can be co-transformed into the *E. coli* strain that does not produce fatty amines (supra) giving strain F18-PU. The host cells can also be transformed with each of the plasmids separately for use as controls giving control strain F18 (pCL1920-CarB-18-cTesA2-13C05) and control strain PU (pACYC-puuE).

The cells can be grown at 32° C. in M9 minimal medium supplemented with 3% (w/v) glucose, 0.5% (v/v) TRITON X-100, 0.1 M bis-tris, pH 7.0, and induced at $OD_{600}$~1.0 with 1 mM isopropyl β-D-1-thiogalactopyranoside (IPTG). At the time of induction, 5 g/L L-glutamate can be added as a source of nitrogen. Strains containing pACYC-puuE can be grown in the presence of the antibiotic carbenicillin (0.05 mg/mL), and strains containing pCL1920-CarB-18-cTesA2-13C05 can be grown in the presence of 0.1 mg/mL spectinomycin in order to select for the respective plasmids. After overnight growth, the cultures of the three strains can be supplemented with an additional 10 g/L glucose and 5 g/L L-glutamate. Aliquots of 1 mL of culture can be frozen at 24 hours post-induction.

In order to prepare samples for analysis, 0.5 mL of ethyl acetate can be added to each aliquot of culture. The samples can then be vortexed at maximum speed for about 15 minutes and centrifuged for 5 minutes as needed. The organic phase can be analyzed with a Gas Chromatograph Mass Spectrometry (GCMS from Agilent 6890) in EI mode (i.e., method: alkane 1 splitless CTC). The F18-PU strain, in which puuE, carB, and/or 'tesA are exogenously expressed, are expected to produce one or more unique peaks that are not observed in either of the PU or F18 negative controls. The expected unique peak in the sample from the F18-PU culture can then be identified via the NIST 05 chemical compound library. An analytical reference standard from Sigma/Aldrich (Product #325163) can be run back to back with the F18-PU sample, in order to confirm the identity of a novel fatty amine compound.

Example 4

Fatty aldehyde precursors and corresponding fatty amines can be generated in vivo by co-expressing an AAR with a GABA aminotransferase (PuuE) along with supplementation of a nitrogen source (glutamate). The fatty aldehyde precursors can be converted into the corresponding amines.

The puuE gene can be cloned from an *E. coli* strain via PCR with a suitable forward and reverse primer (similarly as taught in Example 1, supra). The puuE gene can be ligated into an expression vector (e.g., pACYC, supra), to generate the plasmid pACYC-puuE. A second plasmid can be generated and named pCL1920-aar, which is another expression vector containing the gene for AAR from *Synechococcus elongatus* PCC7942 (aar). The two plasmids can be co-transformed into the *E. coli* strain that does not produce fatty amines (supra) giving strain F19-PU. The host cells can also be transformed with each of the plasmids separately for use as controls giving control strain F19 (pCL1920-aar) and control strain PU (pACYC-puuE).

The cells can be grown at 32° C. in M9 minimal medium supplemented with 3% (w/v) glucose, 0.5% (v/v) TRITON X-100, 0.1 M bis-tris, pH 7.0, and induced at $OD_{600}$~1.0 with 1 mM isopropyl β-D-1-thiogalactopyranoside (IPTG). At the time of induction, 5 g/L L-glutamate can be added as a source of nitrogen. Strains containing pACYC-puuE can be grown in the presence of the antibiotic carbenicillin (0.05 mg/mL) and strains containing pCL1920-aar can be grown in the presence of 0.1 mg/mL spectinomycin, in order to select for the respective plasmids. After overnight growth, the cultures of the three strains can be supplemented with an additional 10 g/L glucose and 5 g/L L-glutamate. Aliquots of 1 mL of culture can be frozen at 24 hours post-induction.

In order to prepare samples for analysis, 0.5 mL of ethyl acetate can be added to each aliquot of culture. The samples can then be vortexed at maximum speed for about 15 minutes and centrifuged for about 5 minutes as needed. The organic phase can be analyzed with a Gas Chromatograph Mass Spectrometry (GCMS from Agilent 6890) in EI mode (i.e., method: alkane 1 splitless CTC). The F19-PU strain, in which puuE, and/or aar are exogenously expressed, are expected to produce a one or more unique peaks that are not observed in either of the PU or F19 negative controls. The expected unique peak in the sample from the F19-PU culture can then be identified via the NIST 05 chemical compound library. An analytical reference standard from Sigma/Aldrich (Product #325163) can be run back to back with the F19-PU sample, in order to confirm the identity of a novel fatty amine compound.

Example 5

Fatty aldehyde precursors and corresponding fatty amines can be generated in vivo by co-expressing a thioesterase (TesA) and a carboxylic acid reductase (CarB) with an amine dehydrogenase (e.g., methylamine dehydrogenase of *Paracoccus denitrificans* or quinohemo protein amine dehydrogenase of *Pseudomonas* spp.) along with supplementation of a nitrogen source (ammonia). The fatty aldehyde precursors can be converted into the corresponding amines.

The amine dehydrogenase (AD) gene from *Paracoccus denitrificans* or *Pseudomonas* spp. can be cloned via PCR with a suitable forward and reverse primer (similarly as taught in Example 1, supra). The AD gene can then be ligated into an expression vector (e.g., pACYC, supra) to generate the plasmid pACYC-AD. A second plasmid can be generated and named pCL1920-CarB-18-cTesA2-13C05, which is another expression vector containing the *Mycobacterium smegmatis* carB gene and a variant of the thioesterase gene ('tesA) from *E. coli* (see Example 1, supra). The two plasmids can be co-transformed into the *E. coli* strain that does not produce fatty amines (supra) giving strain F20-AD. The host cells can also be transformed with each of the plasmids separately for use as controls giving control strain F20 (pCL1920-CarB-18-cTesA2-13C05) and control strain AD (pACYC-AD).

The cells can be grown at 32° C. in M9 minimal medium supplemented with 3% (w/v) glucose, 0.5% (v/v) TRITON X-100, 0.1 M bis-tris, pH 7.0, and induced at $OD_{600}$~1.0 with 1 mM isopropyl β-D-1-thiogalactopyranoside (IPTG). At the time of induction, approximately 0.5-1 g/L ammonia can be added as a source of nitrogen. Strains containing pACYC-AD can be grown in the presence of the antibiotic carbenicillin (0.05 mg/mL) and strains containing pCL1920-CarB-18-cTesA2-13C05 can be grown in the presence of 0.1 mg/mL spectinomycin, in order to select for the respective plasmids. After overnight growth, the cultures of the three strains can be supplemented with an additional 10 g/L glucose and approximately 0.5-1 g/L ammonia. Aliquots of 1 mL of culture can be frozen at 24 hours post-induction.

In order to prepare samples for analysis, 0.5 mL of ethyl acetate can be added to each aliquot of culture. The samples can then be vortexed at maximum speed for about 15 minutes and centrifuged for 5 minutes as needed. The organic phase can be analyzed with a Gas Chromatograph Mass Spectrometry (GCMS from Agilent 6890) in EI mode (i.e., method: alkane 1 splitless CTC). The F20-AD strain, in which AD, carB, and/or 'tesA are exogenously expressed, are expected to produce one or more unique peaks that are not observed in either of the PU or F20 negative controls. The expected unique peak in the sample from the F20-AD culture can then be identified via the NIST 05 chemical compound library. An analytical reference standard from Sigma/Aldrich (Product #325163) can be run back to back with the F20-AD sample, in order to confirm the identity of a novel fatty amine compound.

Example 6

Fatty aldehyde precursors and corresponding fatty amines can be generated in vivo by co-expressing an AAR with an amine dehydrogenase (e.g., methylamine dehydrogenase of *Paracoccus denitrificans* or quinohemo protein amine dehydrogenase of *Pseudomonas* spp.) along with supplementation of a nitrogen source (ammonia). The fatty aldehyde precursors can be converted into the corresponding amines.

The amine dehydrogenase (AD) gene can be cloned from an *E. coli* strain via PCR with a suitable forward and reverse primer (similarly as taught in Example 1, supra). The AD gene can be ligated into an expression vector (e.g., pACYC, supra) to generate the plasmid pACYC-AD. A second plasmid can be generated and named pCL1920-aar, which is another vector containing the gene for AAR from *Synechococcus elongatus* PCC7942 (aar). The two plasmids can be co-transformed into the *E. coli* strain that does not produce fatty amines (supra) giving strain F21-AD. The host cells can also be transformed with each of the plasmids separately for use as controls giving control strain F21 (pCL1920-aar) and control strain AD (pACYC-AD).

The cells can be grown at 32° C. in M9 minimal medium supplemented with 3% (w/v) glucose, 0.5% (v/v) TRITON X-100, 0.1 M bis-tris, pH 7.0, and induced at $OD_{600}$~1.0 with 1 mM isopropyl β-D-1-thiogalactopyranoside (IPTG). At the time of induction, approximately 0.5-1 g/L ammonia can be added as a source of nitrogen. Strains containing pACYC-AD can be grown in the presence of the antibiotic carbenicillin (0.05 mg/mL), and strains containing pCL1920-aar can be grown in the presence of 0.1 mg/mL spectinomycin, in order to select for the respective plasmids. After overnight growth, the cultures of the three strains can be supplemented with an additional 10 g/L glucose and approximately 0.5-1 g/L ammonia. Aliquots of 1 mL of culture can be frozen at 24 hours post-induction.

In order to prepare samples for analysis, 0.5 mL of ethyl acetate can be added to each aliquot of culture. The samples can then be vortexed at maximum speed for about 15 minutes and centrifuged for about 5 minutes as needed. The organic phase can be analyzed with a Gas Chromatograph Mass Spectrometry (GCMS from Agilent 6890) in EI mode (i.e., method: alkane 1 splitless CTC). The F21-AD strain, in which AD and/or aar are exogenously expressed, are expected to produce a one or more unique peaks that are not observed in either of the AD or F21 negative controls. The expected unique peak in the sample from the F21-AD culture can then be identified via the NIST 05 chemical compound library. An analytical reference standard from Sigma/Aldrich (Product #325163) can be run back to back with the F21-AD sample, in order to confirm the identity of a novel fatty amine compound.

As is apparent to one with skill in the art, various modifications and variations of the above aspects and embodiments can be made without departing from the spirit and scope of this disclosure. Such modifications and variations are within the scope of this disclosure.

We claim:

1. A recombinant bacterial cell for production of a fatty amine, wherein the fatty amine has a carbon chain length of between 5 to 24 carbons, comprising:
   (i) one or more expressed genes that encode an exogenous biosynthetic enzyme having thioesterase activity of EC number 3.1.2.-, 3.1.1.5, or 3.1.2.14;
   (ii) one or more expressed genes that encode an exogenous biosynthetic enzyme having carboxylic acid reductase activity of EC number 1.2.99.6; and
   (iii) one or more expressed genes that encode an exogenous biosynthetic enzyme having aminotransferase (EC number 2.6.1) or amine dehydrogenase activity (EC number 1.4.9, 1.4.98, 1.4.99), wherein said recombinant bacterial cell produces the fatty amine in vivo.

2. The recombinant bacterial cell of claim 1, wherein said exogenous biosynthetic enzyme having thioesterase activity converts an acyl-ACP or acyl-CoA to a fatty acid.

3. The recombinant bacterial cell of claim 2, wherein said exogenous biosynthetic enzyme having carboxylic acid reductase activity converts said fatty acid to a fatty aldehyde.

4. The recombinant bacterial cell of claim 3, wherein said exogenous biosynthetic enzyme having aminotransferase or amine dehydrogenase activity converts said fatty aldehyde to a fatty amine.

5. The recombinant bacterial cell of claim 1, wherein said exogenous biosynthetic enzyme having thioesterase activity is encoded by a tesA gene.

6. The recombinant bacterial cell of claim 1, wherein said exogenous biosynthetic enzyme having carboxylic acid reductase activity is encoded by a carB gene.

7. The recombinant bacterial cell of claim 1, wherein said exogenous biosynthetic enzyme having aminotransferase activity is a putrescine or GABA aminotransferase.

8. The recombinant bacterial cell of claim 7, wherein the putrescine aminotransferase is YgjG.

---

SEQUENCE LISTING

```
<160> NUMBER OF SEQ ID NOS: 2

<210> SEQ ID NO 1
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
aggaggaata acatatgaac aggttacctt cgagcgcatc ggc                43

<210> SEQ ID NO 2
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
cccaagcttc gaattcttac gcttcttcga cacttactcg catggcc            47
```

9. The recombinant bacterial cell of claim 8, wherein said YgjG is encoded by an ygjG gene.

10. The recombinant bacterial cell of claim 7, wherein the GABA aminotransferase is PuuE.

11. The recombinant bacterial cell of claim 10, wherein said PuuE is encoded a puuE gene.

12. The recombinant bacterial cell of claim 1, wherein said exogenous biosynthetic enzyme having amine dehydrogenase activity is a methylamine dehydrogenase.

13. The recombinant bacterial cell of claim 12, wherein said methylamine dehydrogenase is from *Paracoccus denitrificans*.

14. The recombinant bacterial cell of claim 1, wherein said recombinant bacterial cell is selected from the group consisting of *Escherichia, Bacillus, Cyanophyta, Lactobacillus, Zymomonas, Rhodococcus*, and *Pseudomonas*.

15. The recombinant bacterial cell of claim 14, wherein said *Escherichia* is *Escherichia coli*.

16. The recombinant bacterial cell of claim 14, wherein said *Cyanophyta* is selected from the group consisting of *Prochlorococcus, Synechococcus, Synechocystis, Cyanothece*, and *Nostoc punctiforme*.

17. The recombinant bacterial cell of claim 14, wherein said *Cyanophyta* is selected from the group consisting of *Synechococcus elongatus* PCC7942, *Synechocystis* sp. PCC6803, and *Synechococcus* sp. PCC7001.

18. A cell culture comprising the recombinant bacterial cell of claim 1.

19. A method of producing a fatty amine, comprising culturing the bacterial cell of claim 1 in a fermentation broth containing a carbon source.

20. The method of claim 19, further comprising harvesting fatty amines that collect in the fermentation broth.

* * * * *